US011559686B2

(12) United States Patent
Swoyer

(10) Patent No.: US 11,559,686 B2
(45) Date of Patent: Jan. 24, 2023

(54) SYSTEMS, DEVICES, COMPONENTS AND METHODS FOR THE DELIVERY OF ELECTRICAL STIMULATION TO CRANIAL NERVES TO TREAT MOOD OR MOOD AFFECTIVE DISORDERS

(71) Applicant: Nextern, Inc., White Bear Lake, MN (US)

(72) Inventor: John Swoyer, Blaine, MN (US)

(*) Notice: Subject to any disclaimer, the term of this patent is extended or adjusted under 35 U.S.C. 154(b) by 0 days.

(21) Appl. No.: 17/013,112

(22) Filed: Sep. 4, 2020

(65) Prior Publication Data
US 2021/0069510 A1 Mar. 11, 2021

Related U.S. Application Data

(60) Provisional application No. 62/896,867, filed on Sep. 6, 2019.

(51) Int. Cl.
*A61N 1/36* (2006.01)
*A61N 1/378* (2006.01)

(52) U.S. Cl.
CPC ..... *A61N 1/36096* (2013.01); *A61N 1/36053* (2013.01); *A61N 1/36057* (2013.01);
(Continued)

(58) Field of Classification Search
CPC ............ A61N 1/36096; A61N 1/36053; A61N 1/36057; A61N 1/3787; A61N 1/36178;
(Continued)

(56) References Cited

U.S. PATENT DOCUMENTS 5,299,569 A * 4/1994 Wernicke ........... A61N 1/36082
607/45
6,366,814 B1 * 4/2002 Boveja ............... A61N 1/36017
607/45
(Continued)

FOREIGN PATENT DOCUMENTS

WO WO-2009018172 A2 * 2/2009 ........... A61N 1/0531

OTHER PUBLICATIONS

Constantin et al., Biocompatibility of Polyimides: A Mini-Review, Materials, 2019, 12, 3166, MDPI.
(Continued)

*Primary Examiner* — Mallika D Fairchild
(74) *Attorney, Agent, or Firm* — Woods Patent Law, P.C.

(57) ABSTRACT

Disclosed are various examples and embodiments of systems, devices, components and methods configured to treat mood disorders in a patient using a compact implantable neurostimulator and corresponding lead(s) that are shaped, sized and configured to be implanted beneath a patient's skin in the head or neck, and to stimulate one or more target cranial nerves. The one or more medical electrical leads comprising electrode(s) are positioned adjacent to, in contact with, or in operative positional relationship to, the one or more target cranial nerves of the patient. In some embodiments, electrical stimulation is provided to the one or more target cranial nerve(s) of the patient for periods of time ranging between 30 and 60 minutes, once or twice per day. In some embodiments, power is provided to the implantable neurostimulator transcutaneously by inductive, wireless, RF, acoustic, microwave, or other suitable non-invasive means.

35 Claims, 18 Drawing Sheets

(52) U.S. Cl.
CPC ..... *A61N 1/36132* (2013.01); *A61N 1/36171* (2013.01); *A61N 1/36178* (2013.01); *A61N 1/3787* (2013.01)

(58) Field of Classification Search
CPC ............ A61N 1/36171; A61N 1/36132; A61N 1/0504; A61N 1/0526; A61N 1/375
See application file for complete search history.

(56) References Cited

U.S. PATENT DOCUMENTS

| | | | |
|---|---|---|---|
| 2005/0165458 A1* | 7/2005 | Boveja | A61N 1/37217 607/45 |
| 2010/0148345 A1* | 6/2010 | Eckhardt | H01L 23/4985 438/653 |
| 2014/0206945 A1* | 7/2014 | Liao | A61N 1/36096 607/45 |
| 2017/0252568 A1* | 9/2017 | Reed | A61N 1/3787 |
| 2020/0139138 A1* | 5/2020 | Sit | H04B 5/0031 |

OTHER PUBLICATIONS

Sun et al., "Assessment of the biocompatibility of photosensitive polyimide for implantable medical device use," J. Biomed. Mater. Res. A., Sep. 1, 2009; 90(3):648-55.

* cited by examiner

SYSTEMS, DEVICES, COMPONENTS AND METHODS FOR THE DELIVERY OF ELECTRICAL STIMULATION TO CRANIAL NERVES TO TREAT MOOD OR MOOD AFFECTIVE DISORDERS

RELATED APPLICATION

This application is related to, and claims priority and other benefits from, U.S. Provisional Patent Application Ser. No. 62/896,867 entitled "Cranial Nerve Stimulation for the Treatment of Mood Disorders and Other Disease States" to Swoyer et al. filed Sep. 6, 2020 (hereafter "the '867 patent application"). The entirety of the '867 patent application is hereby incorporated by reference herein.

FIELD OF THE INVENTION

Various embodiments described and disclosed herein relate to the field of neurostimulation, and more particularly to delivering electrical stimulation therapy to cranial nerves of a patient, including, but not limited to, for the purpose of treating mood disorder and/or mood affective disorders.

BACKGROUND

A variety of therapies are known and have been employed to treat mood disorders and mood affective disorders such as depression, insomnia, and bipolar disorder, most notably the many different types of pharmaceutical drugs that have been developed for such purposes. Pharmaceutical drugs are commonly prescribed for such disorders, but also generally become quite expensive over time, and not uncommonly have significant side effects.

Besides pharmaceutical drugs, other methods have been developed to treat mood and mood affective disorders, such as out-patient or office-based transcranial magnetic stimulation methods to treat depression. Transcutaneous electrical nerve stimulation (TENS) methods to treat depression may also be administered in a patient's home by the patient, where surface electrodes are placed on the exterior of the head and held in place with a temporary adhesive or a device such as a head band. External transcutaneous electrical stimulation of nerves, whether peripheral or cranial, has met with limited and highly uneven and murky degrees of success over the years.

In the field of implantable nerve stimulation devices that have been developed to treat mood disorders such as depression and insomnia, implantable pulse generators employed to effect such treatments have frequently been found to be too large to implant in the head or neck of a patient, and therefore require the use of relatively long medical electrical leads that must be routed from the patient's shoulder or back to a nerve stimulation location in the patien's head or neck.

What is needed are improved and alternative means and methods of treating mood disorder and mood affective disorder patients. The present disclosure is directed to devices, systems, and methods that address one or more deficiencies in the prior art.

SUMMARY

In some embodiments, there is provided an implantable neurostimulator configured to electrically stimulate one or more cranial nerves in a head or neck of a patient to treat a mood disorder or mood affective disorder of the patient, the neurostimulator comprising a housing, at least one medical electrical lead comprising at least one stimulation electrode, pulse generation circuitry operably connected to the lead, and power, energy or electrical charge receiving circuitry operably connected to the pulse generation circuitry and configured to receive power, energy or electrical charge signals transcutaneously from an external power source and external power transmitting circuitry associated therewith, wherein one or more of the pulse generation circuitry, the at least one lead and at least one electrode, and the power receiving circuitry are mounted on or in, or formed as a portion of, one or more flex circuits, and further wherein the pulse generation circuitry, the power receiving circuitry, and at least portions of the one or more flex circuits are disposed within a sealed housing, the implantable neurostimulator is sized, shaped and configured to be implanted in the head or neck of the patient beneath the patient's skin, and the lead and one or more electrodes are sized, shaped and configured to be implanted beneath the patient's skin and positioned adjacent to, in contact with, or in operative positional relationship to, the one or more target cranial nerves.

Such an implantable neurostimulator may further comprise one or more of: (a) the mood or mood affective disorder being one or more of depression, a depressive disorder, insomnia, sadness, mania, bipolar disorder, manic depression, bipolar affective disorder, postpartum depression, seasonal affective disorder (SAD), cyclothymic disorder, premenstrual dysphoric disorder, persistent depressive disorder (dysthymia), disruptive mood dysregulation disorder, depression related to medical illness, and depression induced by substance use or medication; (b) the implantable neurostimulator being configured to electrically stimulate one or more of a facial nerve or portion thereof, a trigeminal nerve or portion thereof, an occipital nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an inferior ganglion branch of the vagus nerve or portion thereof, an olfactory nerve or portion thereof, an optic nerve or portion thereof, an oculomotor nerve or portion thereof, a trochlear nerve or portion thereof, an abducens nerve or portion thereof, a vestibulocochlear nerve or portion thereof, and a spinal accessory nerve or portion thereof; (c) the one or more flex circuits comprising a polyimide substrate; (d) the lead further comprising proximal and distal portions, the proximal portion of the lead being operably connected to the pulse generation circuitry, the at least one electrode being disposed distally from the proximal portion of the lead, the lead comprising one or more electrical conductors operably connecting the at least one electrode to the pulse generation circuitry, the electrical conductors being formed on or in one or more of the lead flex circuits; (e) the sealed housing having a thickness ranging between about 0.1 inches and about 0.4 inches; (f) the sealed housing having a diameter ranging between about 0.05 inches and about 0.8 inches; (g) the sealed housing comprising a flexible polymer configured to conform to at least one of a shape of the patient's skull or overlying skin; (h) the flexible polymer being a thermosettable or shapeable material that can be formed into and will retain a desired shape or curvature; (i) the lead having a length extending beyond the housing ranging between about 0.1 inches and about 4 inches; (j) the lead having a width beyond the housing that ranges between about 0.01 inches and about 0.05 inches; (k) the pulse generation circuitry and the power receiving and storage circuitry being potted within the housing using a medical grade polymer, (1) the at least one lead, the pulse generation circuitry, and the power receiving and storage circuitry being mounted on or in, or formed as a portion of, a single flex circuit or flex circuit substrate; (m) the lead having a length extending beyond the housing ranging between about 0.1 inches and about 4 inches; (n) the power receiving circuitry further comprising electrical charge storage circuitry; (o) the power receiving circuitry further comprising one or more internal induction coils configured to receive electrical power transcutaneously from one or more corresponding external induction coils; (p) the power receiving circuitry further comprising one or more wireless, RF, acoustic, piezoelectric, Thin film bulk wave acoustic resonators (FBAR), microwave energy receiving circuits, and (q) the pulse generation circuitry being configured to deliver stimulation signals comprising one or more of: (1) frequencies ranging between about 2 Hz and about 100 Hz; (2) frequencies ranging between about 2 Hz and about 75 Hz; (3) frequencies ranging between about 4 Hz and about 50 Hz; (4) frequencies ranging between about 5 Hz and about 25 Hz; (5) frequencies ranging between about 7 Hz and about 100 Hz; (6) frequencies ranging between about 100 Hz and about 10,000 Hz; (7) frequencies ranging between about 100 Hz and about 5,000 Hz; (h) frequencies ranging between about 100 Hz and about 2,000 Hz; (8) frequencies ranging between about 100 Hz and about 1,000 Hz; (9) frequencies ranging between about 200 Hz and about 750 Hz; (10) voltages ranging between about 0.1 mV and about 30 V; (11) currents ranging between about 0.1 mA and about 30 mA; (12) pulse widths ranging between about 20 µsec and about 1000 µsec, and (13) durations or periods of time ranging between about 30 seconds and about 2 hours, 5 minutes and about 1 hour, and about 10 minutes and about 45 minutes.

In another embodiment, there is provided a system configured to electrically stimulate one or more cranial nerves in a head or neck of a patient to treat a mood disorder or mood affective disorder of the patient, the system comprising an implantable neurostimulator comprising a housing, at least one medical electrical lead comprising at least one stimulation electrode, pulse generation circuitry operably connected to the lead, and power, energy or electrical charge receiving circuitry operably connected to the pulse generation circuitry and configured to receive power, energy or electrical charge signals transcutaneously from an external power source and external power transmitting circuitry associated therewith, pulse generation circuitry operably connected to the lead, and power or electrical charge receiving circuitry operably connected to the pulse generation circuitry and further configured to receive power signals or electrical charge transcutaneously from an external power source and external power transmitting circuitry associated therewith, wherein one or more of the pulse generation circuitry, the at least one lead and at least one electrode, and the power receiving circuitry are mounted on or in, or formed as a portion of, one or more flex circuits, and further wherein the pulse generation circuitry, the power or charge receiving circuitry, and at least portions of the one or more flex circuits are disposed within a sealed housing, the implantable neurostimulator is sized, shaped and configured to be implanted in the head or neck of the patient beneath the patient's skin, and the lead and one or more electrodes are sized, shaped and configured to be implanted beneath the patient's skin and positioned adjacent to, in contact with, or in operative positional relationship to, the one or more target cranial nerves, an external energy supply device configured to transmit energy transcutaneously through the skin of the patient to the implantable neurostimulator, and a controller or programmer configured to permit a health care provider or the patient to set, adjust, or change at least one of operational and stimulation parameters of the implantable neurostimulator.

Such a system may further comprise one or more of: (a) the external energy supply device comprising one or more batteries and one or more transmitting coils operably connected to the one or more batteries and configured to provide electromagnetic energy transcutaneously to one or more receiving coils included in or operably connected to the power or charge receiving circuitry of the neurostimulator; (b) the external energy supply device comprising wireless, RF, acoustic, piezoelectric, thin film bulk wave acoustic resonator (FBAR), or microwave transmitter circuitry configured to transmit energy transcutaneously through the skin of the patient to the power or electrical charge receiving circuitry of the implantable neurostimulator; (c) the mood disorder or mood affective disorder being treated one or more of depression, a depressive disorder, insomnia, sadness, mania, bipolar disorder, manic depression, bipolar affective disorder, postpartum depression, seasonal affective disorder (SAD), cydothymic disorder, premenstrual dysphoric disorder, persistent depressive disorder (dysthymia), disruptive mood dysregulation disorder, depression related to medical illness, and depression induced by substance use or medication; (d) the system being configured to electrically stimulate one or more of a facial nerve or portion thereof, a trigeminal nerve or portion thereof, an occipital nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an inferior ganglion branch of the vagus nerve or portion thereof, an olfactory nerve or portion thereof, an optic nerve or portion thereof, an oculomotor nerve or portion thereof, a trochlear nerve or portion thereof, an abducens nerve or portion thereof, a vestibulocochlear nerve or portion thereof, and a spinal accessory nerve or portion thereof; (e) the one or more flex circuits comprising a polyimide substrate; (f) the lead further comprising proximal and distal portions, the proximal portion of the lead being operably connected to the pulse generation circuitry, the at least one electrode being disposed distally from the proximal portion of the lead, the lead comprising one or more electrical conductors operably connecting the at least one electrode to the pulse generation circuitry, the electrical conductors being formed on or in one or more of the lead flex circuits; (g) the sealed housing having a thickness ranging between about 0.1 inches and about 0.4 inches; (h) the sealed housing having a diameter ranging between about 0.05 inches and about 0.8 inches; (h) the sealed housing comprising a flexible polymer configured to conform to at least one of a shape of the patient's skull or overlying skin; (i) the flexible polymer being a thermosettable or shapeable material that can be formed into and will retain a desired shape or curvature; (j) the lead having a length extending beyond the housing ranging between about 0.1 inches and about 4 inches; (k) the lead having a width beyond the housing that ranges between about 0.01 inches and about 0.05 inches; (1) the pulse generation circuitry and the power receiving and storage circuitry being potted within the housing using a medical grade polymer (m) the at least one lead, the pulse generation circuitry, and the power receiving and storage circuitry being mounted on or in, or formed as a portion of, a single flex circuit or flex circuit substrate; (n) the lead having a length extending beyond the housing ranging between about 0.1 inches and about 4 inches; (o) the power receiving circuitry further comprising electrical charge storage circuitry; (p) the power receiving circuitry further comprising one or more internal induction coils configured to receive electrical power transcutaneously from one or more corresponding external induction coils, and (q) the power receiving circuitry further comprising one or more wireless, RF, acoustic, piezoelectric, thin film bulk wave acoustic resonators (FBAR), or microwave energy receiving circuits.

In yet another embodiment, there is provided a method of electrically stimulating one or more cranial nerves in a head or neck of a patient to treat a mood disorder or mood affective disorder of the patient, the method comprising providing or implanting beneath the skin of the patient's head or neck an implantable neurostimulator comprising a housing, at least one medical electrical lead comprising at least one stimulation electrode, pulse generation circuitry operably connected to the lead, and power, energy or electrical charge receiving circuitry operably connected to the pulse generation circuitry and configured to receive power, energy or electrical charge signals transcutaneously from an external power source and external power transmitting circuitry associated therewith, wherein one or more of the pulse generation circuitry, the at least one lead and at least one electrode, and the power receiving circuitry are mounted on or in, or formed as a portion of, one or more flex circuits, and further wherein the pulse generation circuitry, the power or charge receiving circuitry, and at least portions of the one or more flex circuits are disposed within a sealed housing, the implantable neurostimulator is sized, shaped and configured to be implanted in the head or neck of the patient beneath the patients skin, and the lead and one or more electrodes are sized, shaped and configured to be implanted beneath the patient's skin and positioned adjacent to, in contact with, or in operative positional relationship to, the one or more target cranial nerves, and electrically stimulating the one or more cranial nerves of the patient with the implantable neurostimulator to treat the mood disorder or mood affective disorder.

Such a method may further comprise one or more of: (a) setting, adjusting, or changing at least one of operational and stimulation parameters of the implantable neurostimulator using a controller or programmer; (b) transmitting energy transcutaneously from an external energy supply device through the skin of the patient to the implantable neurostimulator; (c) tunnelling beneath the patient's skin to form a pocket to receive the implantable neurostimulator and lead therein; (d) the mood disorder or mood affective disorder being treated being one or more of depression, a depressive disorder, insomnia, sadness, mania, bipolar disorder, manic depression, bipolar affective disorder, postpartum depression, seasonal affective disorder (SAD), cyclothymic disorder, premenstrual dysphoric disorder, persistent depressive disorder (dysthymia), disruptive mood dysregulation disorder, depression related to medical illness, and depression induced by substance use or medication; (e) the cranial nerve being electrically stimulated being one or more of a facial nerve or portion thereof, a trigeminal nerve or portion thereof, an occipital nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an inferior ganglion branch of the vagus nerve or portion thereof, an olfactory nerve or portion thereof, an optic nerve or portion thereof, an oculomotor nerve or portion thereof, a trochlear nerve or portion thereof, an abducens nerve or portion thereof, a vestibulocochlear nerve or portion thereof, and a spinal accessory nerve or portion thereof; (f) the pulse generation circuitry delivering stimulation signals comprising one or more of: (1) frequencies ranging between about 2 Hz and about 100 Hz; (2) frequencies ranging between about 2 Hz and about 75 Hz; (3) frequencies ranging between about 4 Hz and about 50 Hz; (4) frequencies ranging between about 5 Hz and about 25 Hz; (5) frequencies ranging between about 7 Hz and about 100 Hz; (6) frequencies ranging between about 100 Hz and about 10,000 Hz; (7) frequencies ranging between about 100 Hz and about 5,000 Hz; (h) frequencies ranging between about 100 Hz and about 2,000 Hz; (8) frequencies ranging between about 100 Hz and about 1,000 Hz; (9) frequencies ranging between about 200 Hz and about 750 Hz; (10) voltages ranging between about 0.1 mV and about 30 V; (11) currents ranging between about 0.1 mA and about 30 mA; (12) pulse widths ranging between about 20 μsec and about 1000 μsec, and (13) durations or periods of time ranging between about 30 seconds and about 2 hours, 5 minutes and about 1 hour, and about 10 minutes and about 45 minutes.

Further embodiments are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Figure 1:
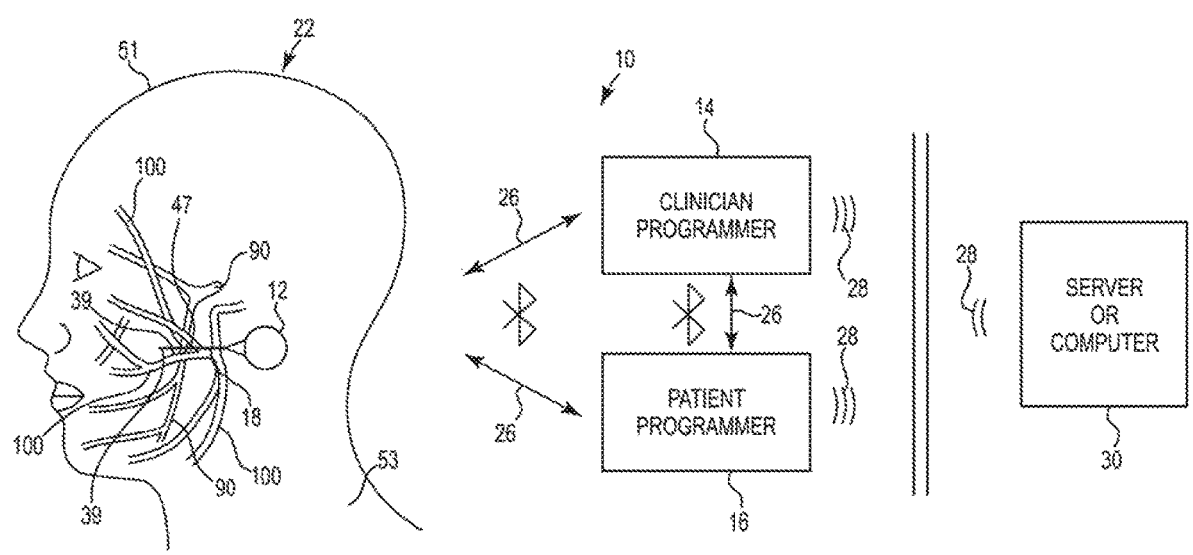
FIG. 1 shows a block diagram of one embodiment of a cranial nerve stimulation system 10.

Described herein are various embodiments of systems, devices, components and methods for treating mood disorders and mood affective disorders in a patient using cranial nerve neurostimuation techniques.

Examples of mood disorders and mood affective disorders that may be treated with the cranial nerve electrical stimulation systems, devices, components and methods disclosed and described herein include, but are not limited to, one or more of depression, a depressive disorder, insomnia, sadness, mania, bipolar disorder, manic depression, bipolar affective disorder, postpartum depression, seasonal affective disorder (SAD), cyclothymic disorder, premenstrual dysphoric disorder, persistent depressive disorder (dysthymia), disruptive mood dysregulation disorder, depression related to medical illness, and depression induced by substance use or medication.

Examples of cranial nerves that may be electrically stimulated using the systems, devices, components and methods disclosed and described herein include, but are not necessarily limited to, one or more of a facial nerve or portion thereof, a trigeminal nerve or portion thereof, an occipital nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an inferior ganglion branch of the vagus nerve or portion thereof, an olfactory nerve or portion thereof, an optic nerve or portion thereof, an oculomotor nerve or portion thereof, a trochlear nerve or portion thereof, an abducens nerve or portion thereof, a vestibulocochlear nerve or portion thereof, and a spinal accessory nerve or portion thereof.

In one embodiment, and with general reference to FIGS. 1 through 7, implantable neurostimulator 12 is configured to electrically stimulate one or more cranial nerves 80 in a head or neck of a patient to treat a mood disorder or mood affective disorder of the patient. Implantable neurostimulator 12 comprises housing 31, at least one medical electrical lead 18 comprising at least one stimulation electrode 39, pulse generation circuitry 34 operably connected to lead 18, power, energy or electrical charge receiving circuitry 40 operably connected to pulse generation circuitry 34, and control circuitry 36. In one embodiment, power, energy or electrical charge receiving circuitry 40 is configured to receive power, energy or electrical charge signals transcutaneously from an external power source and external power transmitting circuitry associated therewith. One or more of pulse generation circuitry 34, at least one lead 18 and at least one electrode 39, and power receiving circuitry 40 are mounted on or in, or formed as a portion of, one or more flex circuits 37.

Pulse generation circuitry 34, power receiving circuitry 40, and at least portions of one or more flex circuits 37 are disposed within sealed housing 31, which may or may not be hermetically sealed. Hermetic sealing of housing 31, if desired, may be accomplished in a number of ways, such as by disposing a hermetic coating or layer over the interior or exterior surfaces of housing 31, or forming housing 31 out of a suitable malleable, bendable, or shapeable metal or metal alloy. The components and circuitry disposed inside housing 31 may also be sealed and potted therein using epoxy, silicone, a polymer, or other suitable materials. Implantable neurostimulator 12 is sized, shaped and configured to be implanted in the head 51 or neck 53 of the patient beneath the patient's skin 153, and lead 18 and one or more electrodes 39 are sized, shaped and configured to be implanted beneath the patient's skin 153 and positioned adjacent to, in contact with, or in operative positional relationship to, one or more target cranial nerves 80.

FIG. 1 shows a block diagram of one embodiment of a cranial nerve stimulation system 10, which as shown comprises implantable stimulator (IS) 12 including one or more medical electrical leads 18, clinician programmer (CP) 14, patient programmer (PP) 16, and central server, remote computer, and/or local computer 30. Other components of system 10 are also contemplated, more about which is said below. IS 12 includes one or more leads 18 to which the circuitry internal of IS 12 is operably connected. In the Figures, only one such lead 18 is shown, although 2, 3 or more medical electrical leads can also be included in IS 12 or operably connected thereto. Thus, IS 12 contains or is operably connected to the proximal ends 57 of one or more medical electrical leads 18, which according to one embodiment are implantable leads configured for chronic placement beneath a patient's skin 153, near or in proximity to a desired cranial nerve 80 or bundle of cranial nerves that are then to be electrically stimulated under the control of IS 12. In some embodiments, IS 12 features operational and/or stimulation parameters that can be programmed, and in other embodiments such parameters are predetermined or predetermined but selectable form a memory of control circuitry 36, as further described below. In the embodiment shown in FIG. 1, distal end 47 of lead 18 is situated near a branch of facial nerve 100 and provides electrical stimulation signals originating from IS 12 to or near, by way of non-limiting example, such cranial nerve. Other cranial nerves may also be stimulated by system 10, as further described below.

Figure 7:
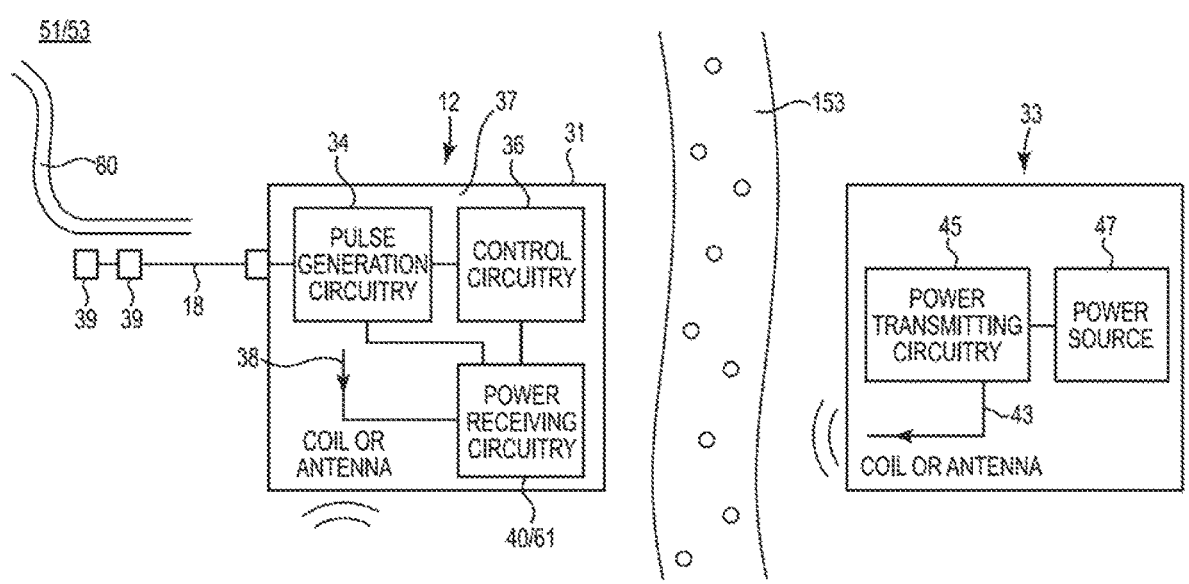
FIG. 7 shows a functional block diagram of IS 12 implanted within a patient and external device 33 located outside the patient and in communication therewith transcutaneously.

In some embodiments, the electrical stimulation parameters, therapy delivery, and/or operational parameters of IS 12 may be programmed by CP 14 under the control of a physician or other health care provider and/or may be stored and preprogrammed in a memory of IS 12 (included, for example, in control circuitry 36—see FIG. 7). Optional PP 16 operates under the control of patient 22, and may be configured to permit patient 22 to turn IS 12 on or off, to change electrical stimulation parameters (in some embodiments within certain limits), or to effect other changes in the operation of IS 12. In one embodiment, CP 14 is configured to permit a physician or other health care provider to program PP 16 via wireless or other communication and connection means (e.g., Bluetooth, RF, telemetry, inductive or magnetic coupling, cable, etc.) 26. Remote or local server or computer 30 may be configured to receive and/or transmit data, programming instructions, and the like from and to CP 14 and/or PP 16, as well as to process, analyze, and facilitate interpretation of such data.

Figure 2:
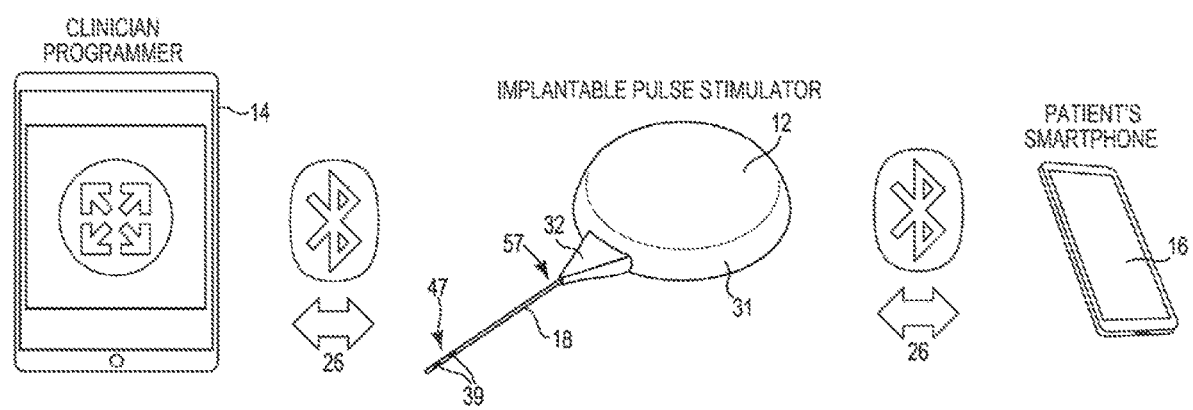
FIG. 2 shows a block diagram of another embodiment of cranial nerve stimulation system 10.

FIG. 2 shows a block diagram of another embodiment of a peripheral nerve stimulation system 10, which as shown comprises implantable neurostimulator (IS) 12 comprising housing 31, and transition component or protective covering 32, which can be configured to cover and protect the transition between circuitry contained within 1S 12 such as pulse generation circuitry 34 and proximal end 57 of lead 18, thereby to permit lead 18 to be more both more flexible and more robust at its proximal end 57. Lead 18 comprises proximal end 57, distal end 47, and one or more electrodes 39.

Figure 3:
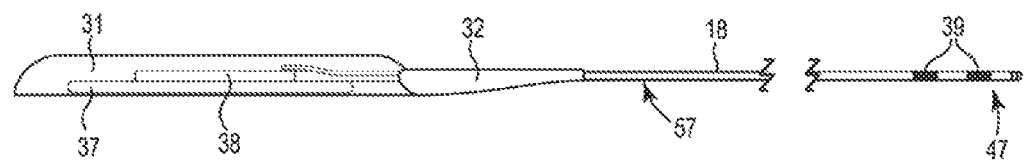
FIG. 3 shows a top view of one embodiment of implantable stimulator (IS) 12.
Figure 4:
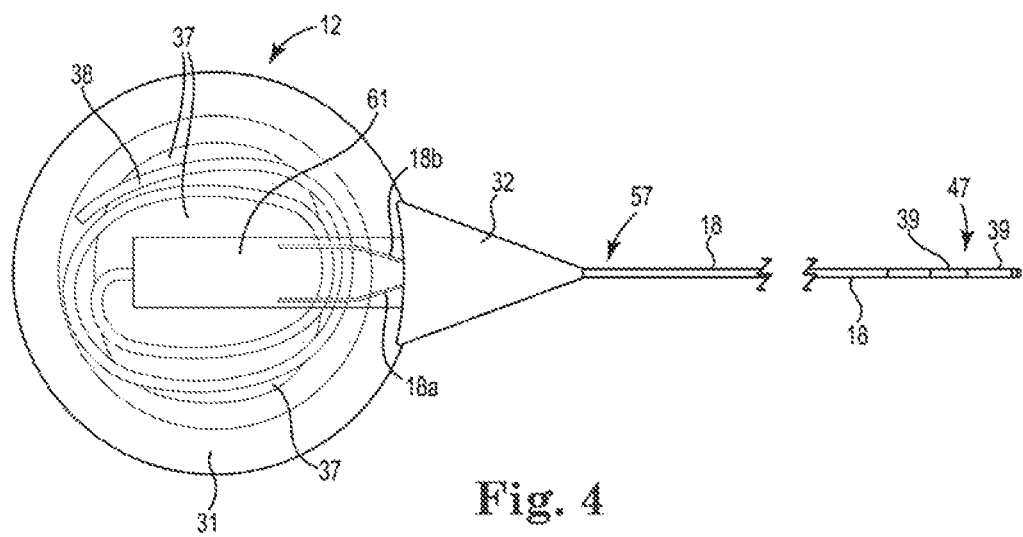
FIG. 4 shows a side view of IS 12 from FIG. 3.

In the embodiments of IS 12 shown in FIGS. 3 and 4, bipolar electrodes (or a set of two electrodes) 39 are shown, although other configurations of electrodes for lead(s) 18 are also contemplated, such as unipolar electrodes, tri-polar electrodes, and more. See FIG. 10 and the discussion corresponding thereto below.

In some embodiments, IS 12 includes a conventional connector block to which the proximal ends of one or more lead(s) 18 and/or lead extensions are connected. In other embodiments, as shown in FIGS. 1-7, a single lead 18 forms a portion of IS 12 and no connector block is required. In still other embodiments, multiple leads 18 form a portion of IS 12 and no connector block is also required.

In embodiments of IS 12 where no connector block is required, flex circuits 37 can be employed to form a single flexible substrate upon which lead conductor traces are disposed between the output stages of pulse generation circuitry 34 and electrodes 39, and further upon which pulse generation circuitry 34, power receiving circuitry 40/communication interface 61, and coil and/or antenna are also formed or to which such circuitry is operably connected. Such a configuration of flex circuit 37 imparts increased mechanical robustness, reliability, and flexibility to the substrate of flex circuit 37, and further aids in the miniaturization of IS 12.

Continuing to refer to FIG. 2, CP 14 is shown as a tablet device configured to communicate wirelessly (e.g., via Bluetooth) with IS 12 and/or patient 22's PP 16 (which as shown in FIG. 2 is a smart phone). In some embodiments, PP 16 is configured to permit patient 22 to activate, deactivate, program and/or adjust the electrical stimulation parameters and operation of IS 12. As further shown in FIG. 2, bipolar lead 18 may be employed in system 10; other numbers and types of medical electrical leads are contemplated for use in system 10 (as discussed briefly above and in further detail below).

Figure 5:
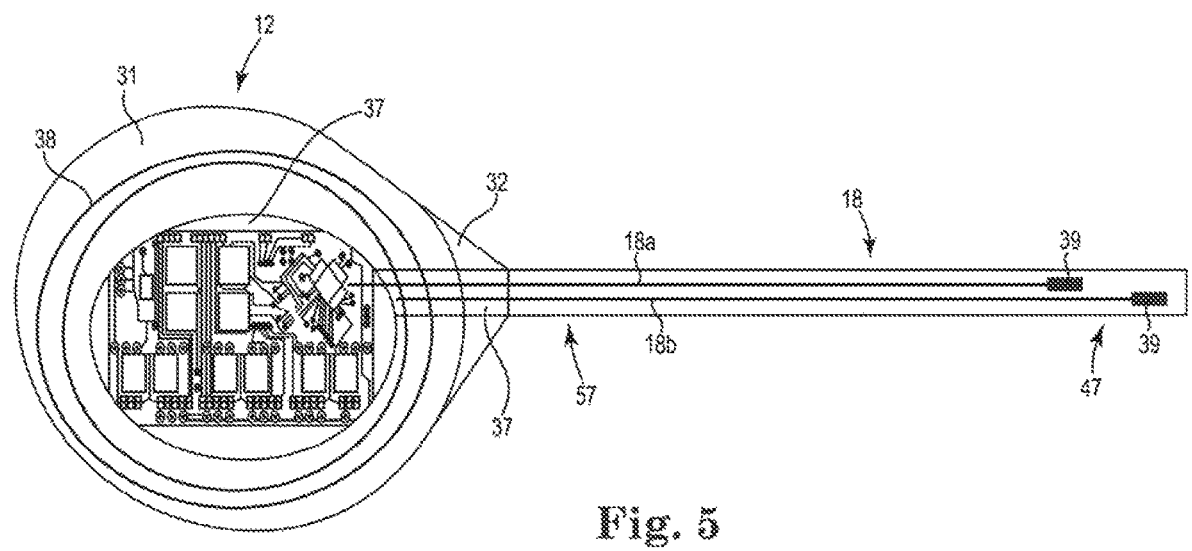
FIG. 5 shows a top view of another embodiment of IS 12.
Figure 6:
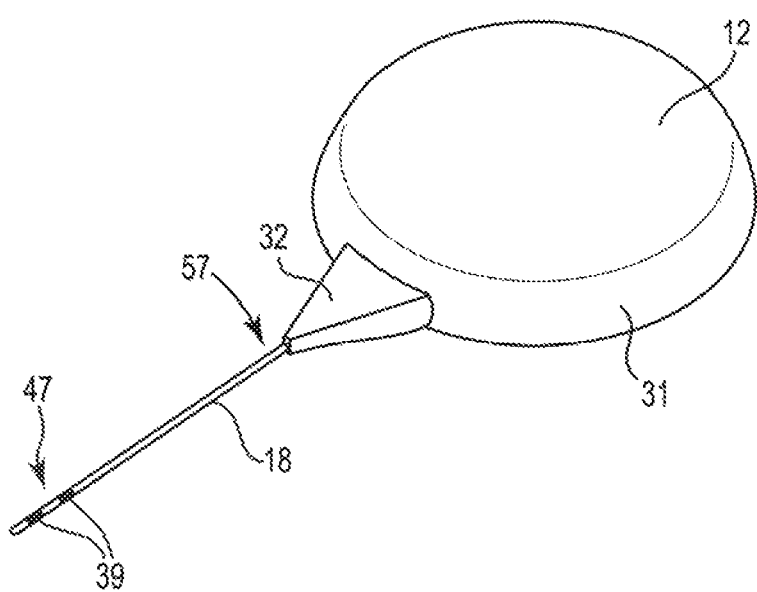
FIG. 6 shows a top right perspective view of IS 12 from FIGS. 3 and 4.

FIGS. 3, 4 and 5 show side, top, and top see-through or semi-transparent views, respectively, of various portions of one embodiment of IS 12. FIG. 6 shows a top perspective view of one embodiment of IS 12.

FIG. 7 shows a block diagram of one embodiment of IS 12 implanted beneath the skin 153 of a patient, with lead 18 and electrodes 39 thereof positioned near a cranial nerve 80 to provide electrical stimulation thereto. External power transmitting device 33 is configured to provide power, energy or charge transcutaneously to IS 12, and may also be configured to communicate with IS 12 in a manner similar to that of PP 16. In some embodiments, PP 16 includes the functionality of external power transmitting device 33. In other embodiments, external device 33 is configured to transfer power, energy or charge to IS 12 so that it may operate and stimulate a given cranial nerve 80, or so that it may charge a capacitor or battery in IS 12, or both. In still further embodiments, power receiving circuitry 40/61 can comprise one or more of electrical charge storage circuitry, one or more internal induction coils configured to receive electrical power transcutaneously from one or more corresponding external induction coils, or one or more wireless, RF, acoustic, piezoelectric, thin film bulk wave acoustic resonators (FBAR), microwave energy receiving circuits.

Referring now to FIG. 3, there is shown a side view of IS 12 comprising housing 31, antenna or coil 38, flex circuit 37, lead protective cover 32, lead 18, distal end of lead 47, proximal end of lead 57, and bi-polar electrodes 39. FIG. 4 shows a top view of IS 12 with the same components shown in FIG. 3, and also showing coil or antenna 38, which terminates in power receiving circuitry 40 and communications interface 61. Per FIG. 7, power receiving circuitry 40 and communications interface 61 are operably connected to pulse generation circuitry 34 and control circuitry 36. Circuitry 34, 40, 61, and 36 and antenna or coil 38 are shown disposed atop and operably connected to flex circuit 37, but in alternative embodiments may be formed directly into or upon flex circuit 37 and its corresponding substrate, or some such components may be disposed atop, beside, or underneath flex circuit 37 while others of such components may be formed directly into or upon flex circuit 37.

As shown in FIGS. 4 and 5, lead conductors 18a and 18b are routed from the output stages of pulse generation circuitry 34 to flex circuit 37 and its corresponding substrate along lead 18 for electrical connection to electrodes 39. In one embodiment, flex circuit 37 forms a substrate that includes and/or has disposed in or on it the circuitry shown in IS 12 of FIG. 7. In some embodiments, the same substrate or single piece of flex circuit 37 is used to form a substrate for lead 18. Flex circuit 37 may also be divided into different pieces or portions of flex circuit material that are electrically and operably connected to one another using appropriate electrical connection means and methods known in the art.

In some embodiments, flex circuit 37 comprises polyimide or KAPTON®, and has electrical circuitry disposed thereon by, for example, vapor deposition or other thin film electrical circuitry forming and manufacturing techniques, and can include traces or electrical conductors, transistors, capacitors, inductors, logic circuitry, and so on. For further information regarding biocompatible polyimides and KAPTON, see, for example: (a) Biocompatibility of Polyimides: A Mini-Review" to Constantin et al, in *Materials,* 2019, 12, 3166; doi:10.3390/ma12193166 ("the Constantin reference"), and (b) "Assessment of the biocompatibility of photosensitive polyimide for implantable medical device use" to Sun et al., J. Biomed. Mater. Res. A., 2009 Sep. 1; 90(3):648-55. doi: 10.1002/bm.a.32125 ("the Sun reference"). The Constantin and Sun references are hereby incorporated by reference herein, each in its respective entirety pursuant to copies of both publications being submitted in an Information Disclosure Statement to the USPTO on even date herewith.

In some embodiments, ASICs or other integrated circuits are employed to provide the functionalities and operations of circuitry 34, 36, 38, 40, and/or 61 shown in FIGS. 3, 4, 5 and 7, and may be mounted on or operably connected to flex circuit 37 using, for example, flip chip techniques. FIG. 5 shows one such embodiment, where circuitry 34, circuitry 36, circuitry 38, circuitry 40, and/or circuitry 61 (which in most embodiments are integrated circuits) are mounted on flex circuit 37.

Antenna or coil 38 can assume various different configurations as shown in FIGS. 4 and 5. In one embodiment, a first purpose of antenna or coil 38 may be to receive power, charge, or energy from an external device 33 and employ such power, charge, or energy to operate the various electrical and electronic components of IS 12. A second purpose of antenna or coil 38 can be to provide communication functionality between IS 12 and an external device such as device 33 (see FIG. 7), CP 14, and/or PP 16. In some embodiments, antenna or coil 38 is configured to receive and/or transmit data, information, and/or instructions from and/or to external devices such as CP 14, PP 16, and/or external device 33. In other embodiments, antenna or coil 38 is configured to receive electrical or other power from an external device and has limited or no communication abilities. Thus, the communication capabilities and functionality of IS 12 may be "primitive" or limited, or may be sophisticated, depending on how small or large IS 12 is to be, and also on the operational complexity of the specifications or objectives of IS 12 that are to be achieved.

For example, in one embodiment IS 12 is configured to deliver to electrical stimulation pulses through lead 18 and electrodes 39 only when an external power source is positioned directly over or very close to IS 12, and energy is transferred transcutaneously to coil or antenna 38, thereby triggering and maintaining the operation of pulse generation circuitry 34 only so long as the external power source is held in sufficiently close proximity to coil or antenna 38 of IS 12. In such an embodiment, no battery or only a very small battery, capacitor or charge buffer may be required in IS 12. In other embodiments which will necessarily be larger and less compact, IS 12 contains a rechargeable battery that can provide the electrical power necessary to operate IS 12 after an overlying recharging coil or other device has been withdrawn from a charging position over coil or antenna 38. In still another embodiment, IS 12 contains a primary battery that provides the electrical power necessary to operate IS 12 for a limited duration of time that may extend over days, weeks, months or years, depending on the charge capacity of the primary battery and other factors.

Referring now to FIGS. 2 through 5, in some embodiments sealed housing 31 may have a thickness ranging between about 0.1 inches and about 0.4 inches, a diameter ranging between about 0.05 inches and about 0.8 inches, and lead(s) 18 may have a length extending beyond housing 31 ranging between about 0.1 inches and about 4 inches, and/or a width beyond the housing that ranges between about 0.01 inches and about 0.05 inches.

Referring to FIGS. 3-5 and 7, pulse generation circuitry 34, control circuitry 36, and power receiving and storage circuitry 36 may be potted within housing 31 using, for example, a medical grade polymer.

Referring to FIGS. 3-6, at least one lead 18, pulse generation circuitry 34, control circuitry 36, and power receiving and storage circuitry 40/61 may be mounted on or in, or formed as a portion of, a single flex circuit or flex circuit substrate 37. Power receiving circuitry 40/61 may further comprise electrical charge storage circuitry, one or more internal induction coils configured to receive electrical power transcutaneously from one or more corresponding external induction coils, and/or one or more wireless, RF, acoustic, piezoelectric, Thin film bulk wave acoustic resonators (FBAR), microwave energy receiving circuits.

With reference to FIG. 7, in some embodiments pulse generation circuitry 34 may be configured to deliver stimulation signals comprising one or more of: (1) frequencies ranging between about 2 Hz and about 100 Hz; (2) frequencies ranging between about 2 Hz and about 75 Hz; (3) frequencies ranging between about 4 Hz and about 50 Hz; (4) frequencies ranging between about 5 Hz and about 25 Hz; (5) frequencies ranging between about 7 Hz and about 100 Hz; (6) frequencies ranging between about 100 Hz and about 10,000 Hz; (7) frequencies ranging between about 100 Hz and about 5,000 Hz; (h) frequencies ranging between about 100 Hz and about 2,000 Hz; (8) frequencies ranging between about 100 Hz and about 1,000 Hz; (9) frequencies ranging between about 200 Hz and about 750 Hz; (10) voltages ranging between about 0.1 mV and about 30 V; (11) currents ranging between about 0.1 mA and about 30 mA; and (12) pulse widths ranging between about 20 μsec and about 1000 μsec. Pulse generation circuitry 34 may further be configured to deliver stimulation signals over periods of time ranging between about 30 seconds and about 2 hours, 5 minutes and about 1 hour, and about 10 minutes and about 45 minutes. Other frequencies, amplitudes, and durations for electrical nerve stimulation are also contemplated.

In some embodiments, and with reference to FIG. 7, external device may be fitted to an adhesive substrate or bandage that patient 22 may wear on or attach to the surface of skin 153 while IS 12 is being powered transcutaneously and/or while IS 12 is electrically simulating a target cranial nerve 80, or while IS 12 is being recharged. Alternatively, external device 33 may be affixed or attached to a headband or head strap that is configured to hold external device 33 on patient's skin 153 in a location and position that permits appropriate or suitable power of signal coupling between IS 12 and external device 33 to occur.

Figure 8:
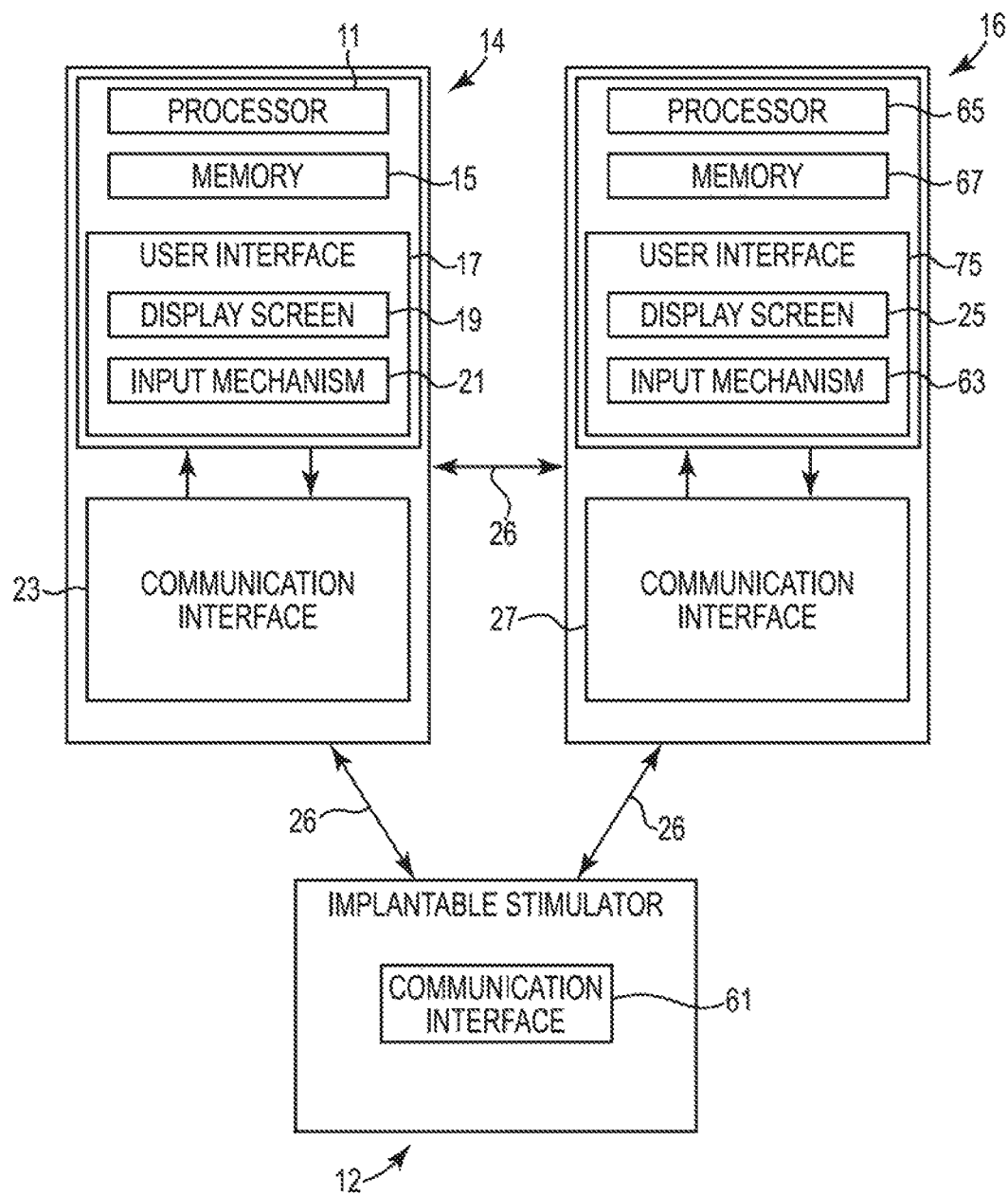
FIG. 8 shows one embodiment of block diagrams for CP 14, PP 16, and IS 12.

FIG. 8 shows one embodiment of block diagrams for CP 14, PP 16, and IS 12, with a focus on communications that can occur in some embodiments between such components of system 10. As shown in FIG. 8, Bluetooth or other communication means 26 may be employed for communication between system components 14, 16, and 12. CP 14 includes processor or CPU 11, memory 15, which among other things stores programming instructions and control instructions to operate and control IS 12, and user interface 17, which can include a screen 19 and an input mechanism 21 (e.g., keypad, microphone, buttons, etc.). Communication interface 59 is configured to permit wireless or wired communications with IS 12 and/or PP 16. Communication interface 61 is configured to communicate wirelessly or in a wired manner with CP 14 and/or PP 16. PP 16 comprises display screen 25, communication interface 27, and input mechanism 63.

Figure 9:
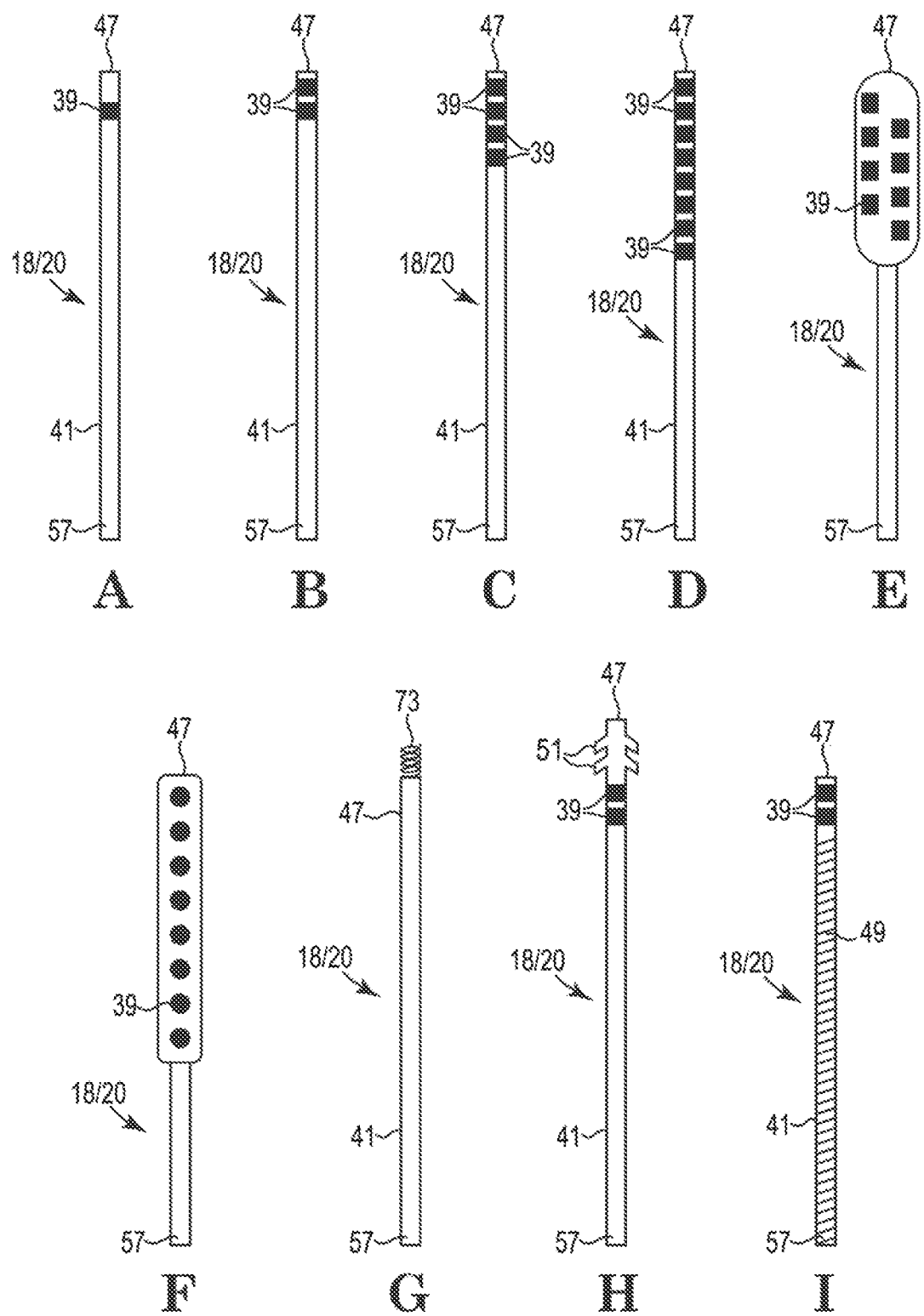
FIG. 9 shows various embodiments of medical electrical leads 18 that may be utilized in at least some embodiments of system 10.

FIG. 9 shows various embodiments of medical electrical leads 18 that can be utilized in at least some embodiments of system 10. The various embodiments of medical electrical leads 18 and/or 20 shown in FIG. 10 include the following:

- Lead A—a unipolar lead with a lead body 41 and a single electrode 39 disposed near its distal end 47;
- Lead B—a bipolar lead with a lead body 41 and two electrodes 39 disposed near its distal end 47;
- Lead C—a quadripolar lead with a lead body 41 and four electrodes 39 disposed near its distal end 47;
- Lead D—an octopolar lead with a lead body 41 and eight electrodes 39 disposed near its distal end 47;
- Lead E—a paddle lead with a lead body 41 and a plurality of paddle electrodes 39 disposed in two columns;
- Lead F—a paddle lead with a plurality of electrodes 39 disposed in a single column;
- Lead G an active fixation lead with a helically wound wire coil 49 disposed at its distal end 47, where coil 49 serves both as a fixation device 49 and an electrode 39;

Lead H—a tined lead with one or more flexible or deformable tines 57 disposed near its distal end 47; and Lead I—a bipolar lead with a lead body 41 and two electrodes 39 disposed near its distal end 47. In some embodiments, cuff electrode leads may also be employed, as is known in the neurostimulation arts.

Other non-limiting examples of medical electrical leads 18 suitable for use in some embodiments of IS 12 include leads used in conjunction with one or more ground electrodes, leads having arrays of cathodes employed in various configurations respecting corresponding anodes (all serving as electrodes 39), wire electrodes 39, hook-shaped electrodes 39, and barb-shaped electrodes 39. In a case where a lead 18 comprises three or more electrodes 39, IS 12 can be configured to controllably switch and control one or more specific pairs or other groupings of electrodes 39 to which electrical stimulation is delivered in various combinations as anodes and/or cathodes. Likewise, pairs or other groups of electrodes 39 in different leads 18 (by way of non-limiting example) can be controllably switched or controlled so that the electrical fields emitted by electrodes 39 extend at least some distance between the different leads 18 and 20. In such a manner, optimum electrode pairings or groupings tailored to the specific patient 22, lead(s) placement, nerve location, etc., can be achieved to deliver the best therapy to patient 22.

In some embodiments, each of leads 18 comprises at least one cathode (electrode 39) that can be placed near a portion of the target cranial nerve 80. Alternatively, more than one cathode (electrode 39) can be utilized. As one of the electrodes is being used as a cathode for stimulation, the other electrode can be used as an anode for a return path to complete the electrical circuit. Alternatively, both stimulation electrodes could utilize a(n) additional electrode(s) as the anode. This anode could be on the one or more leads 18 described above, a separate lead 18, or an external ground pad or other grounding device.

The lead examples and embodiments shown in FIG. 6 are not intended to be limiting or exhaustive, but are merely illustrative of different types of leads that can be employed in system 10. Other types and configurations of medical electrical leads other than those shown in FIG. 6 are contemplated, including various permutations and combinations of the different lead elements and components shown in FIG. 9.

Figure 10:
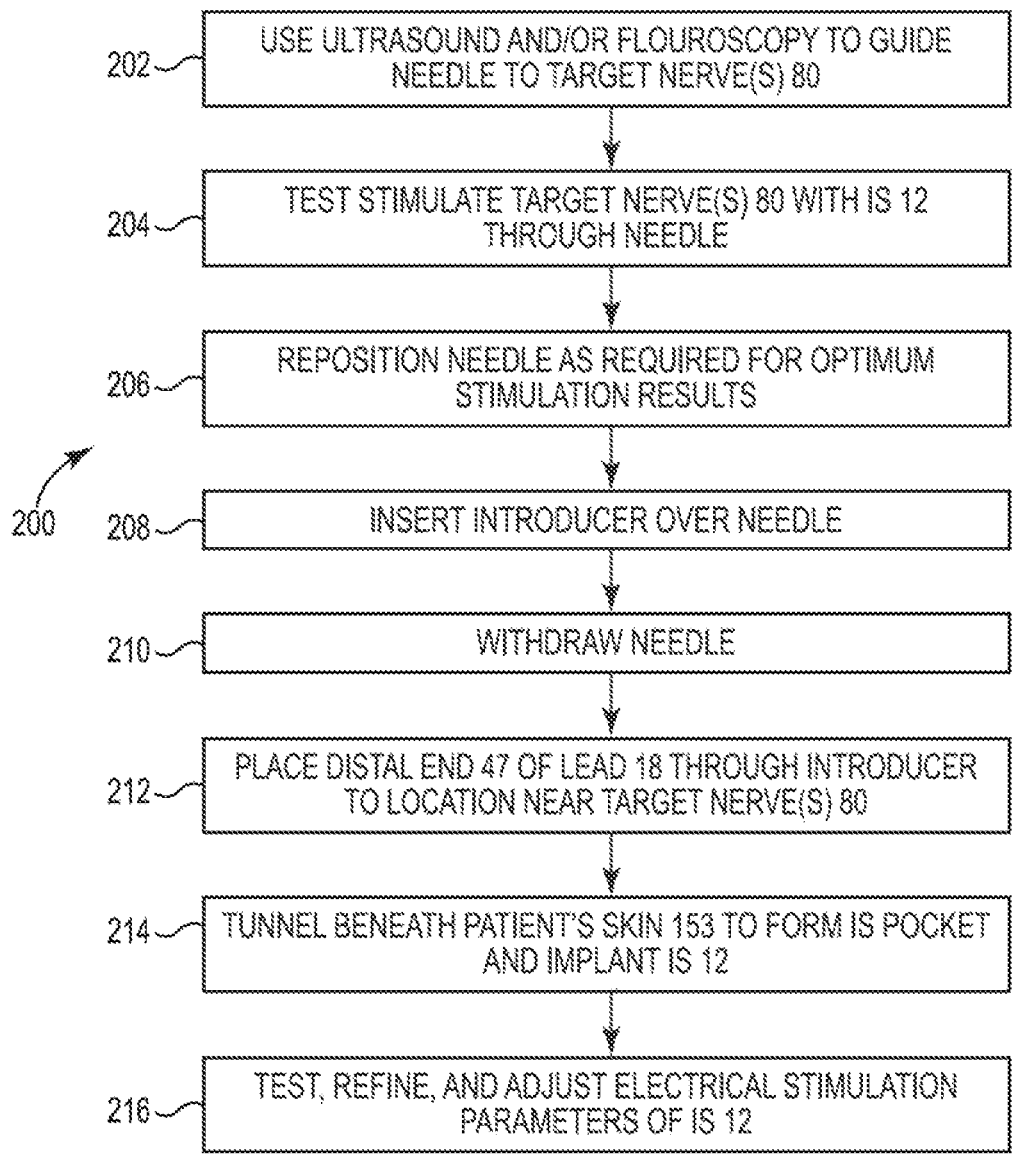
FIG. 10 shows one embodiment of a method 200 for implanting IS 12 in a patient.

FIG. 10 shows one embodiment of method 200 of implanting IS 12 and corresponding/included lead 18(*s*) in a patient for the purpose of delivering mood or mood affective disorder therapy to a patient by means of cranial nerve electrical stimulation. In step 202, ultrasound, fluoroscopic, MRI, PET scan, and/or CT scan techniques, or any other suitable imaging techniques, are employed to guide a test stimulation needle(s) to appropriate locations near one or more cranial target nerves (see, e.g., FIGS. 14-20). By way of non-limiting example, in one embodiment, needle(s) is/are guided to appropriate target nerve locations, which as described below are in suitably close proximity to the one or more target cranial nerves 80.

Once one or both needle(s) have been guided to a desired location near the one or more target cranial nerves 80 of interest, at step 204 target nerve(s) 80 are electrically stimulated by operably attaching the proximal ends of the needles to an external pulse generator and activating a desired output stimulation pattern or regime for delivery to the needles. Different stimulation parameters can be tested at this time by varying any one or more of the voltage, current, frequency, pulse width, amplitude, overlap, interleaving, and delivery of the stimulation signals, as well as other electrical stimulation parameters.

In addition to experimenting with different stimulation parameters, the needles can be repositioned or their locations changed as required or desired at step 206 so that optimum stimulation results are obtained (e.g., maximum, sufficient, or acceptable mood or mood affective disorder therapy in response to test stimulation signals). Once step 206 has been completed, at step 208 an introducer may be inserted over each needle, and at step 210 the needle(s) are withdrawn from the patient. Distal ends 47 of lead(s) 18 are then inserted through the introducers to their respective target nerve locations at step 212. Alternatively, the needles are hollow needles having inner diameters sufficiently large (e.g., 2 mm or more) to accept therein lead(s) 18 having diameters less than the inner diameters of the needles. Other techniques for implanting lead(s) 18 are also contemplated.

At step 214, further refinement and adjustment of electrical stimulation and programming instructions may then be carried out at step 116.

As an example, patient 22 with a mood or mood affective disorder is implanted with a lead(s) 18 near one or more appropriate target cranial nerves 80. The one or more appropriate nerve targets are identified using percutaneous needle sticks, and demonstrating activation of the target nerve as viewed using an ultrasound apparatus. Once the target nerve and location have been established, lead(s) 18 are inserted using standard techniques. System 10 and IS 12 are then programmed using a clinician programmer app in CP 14 to determine appropriate stimulation parameters (e.g., amplitude, frequency, pulse width, duration of electrical stimulation, etc.) for patient 22.

In addition, an MRI can be used to image one or more cranial nerves in the patient to assess the precise and optimal locations for lead placement before lead(s) 18 are implanted in patient 22. An MRI may also be used to image one or more cranial nerves 80 in patient 22 after therapy has been delivered to patient 22 by nerve stimulation signals, and after the lead(s) have been implanted in patient 22.

Figure 11:
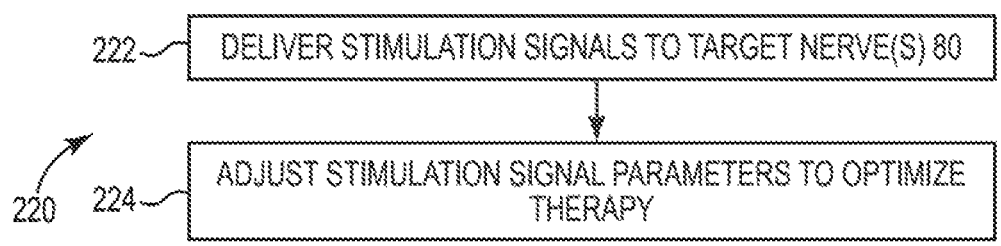
FIG. 11 shows one embodiment of a method 220 for delivering and adjusting stimulation signals delivered to one or more target cranial nerves pf a patient.

Referring now to FIG. 11, there is shown one embodiment of a method 220 of electrically stimulating a patient using an implantable cranial nerve stimulation system 10 as described herein. At step 222, stimulation signals are delivered to one or more target cranial nerves 80. At step 224, nerve stimulation signal parameters are adjusted to optimize the therapy that is being delivered to patient 22 for the mood or mood affective disorder.

Methods other than 200 and 220 are contemplated for testing stimulation and implanting stimulator 12.

Figure 12:
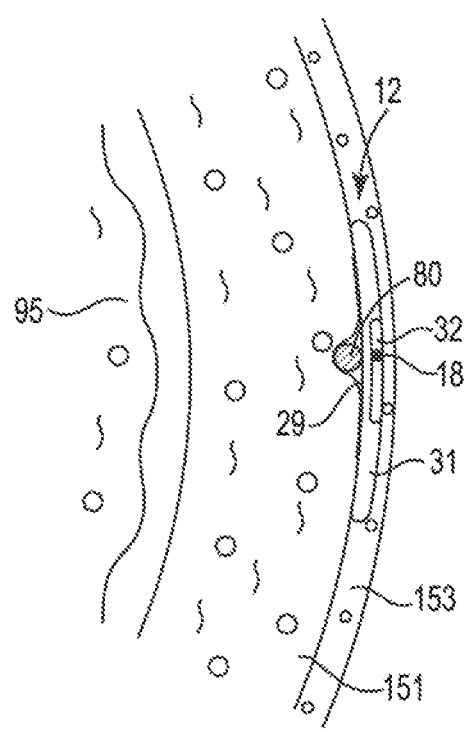
FIG. 12 shows a cross-sectional view of one embodiment of IS 12 implanted beneath a patient's skin 153 adjacent a patient's skull 155.

FIG. 12 shows a cross-section view of one embodiment of IS 12 implanted beneath a patient's skin 153 adjacent a patient's skull 155. As shown, bottom surface 29 of housing 31 is curved and conforms generally to the curvature and shape of skull 151. Such a curved configuration of IS 12 so that it conformably engages and fits along the shape and outline of skull 151 helps prevent erosion of or damage to patient's skin 153, and also increases the degree of comfort patient 12 experiences while having IS 12 implanted in his or her head or neck. Sealed housing 21 can comprise a flexible polymer that is configured to conform to at least one of a shape of the patient's skull 151 or overlying skin 153. The flexible polymer of housing 31 may be a thermosettable or shapeable material that can be formed into and will retain a desired shape or curvature. Such forming or shaping can be carried out by a health care provider during the implantation of IS 12 using, for example, a form that has been preconfigured to the appropriate shape or curvature of the patient's skull; 151 or skin 153.

Figure 13:
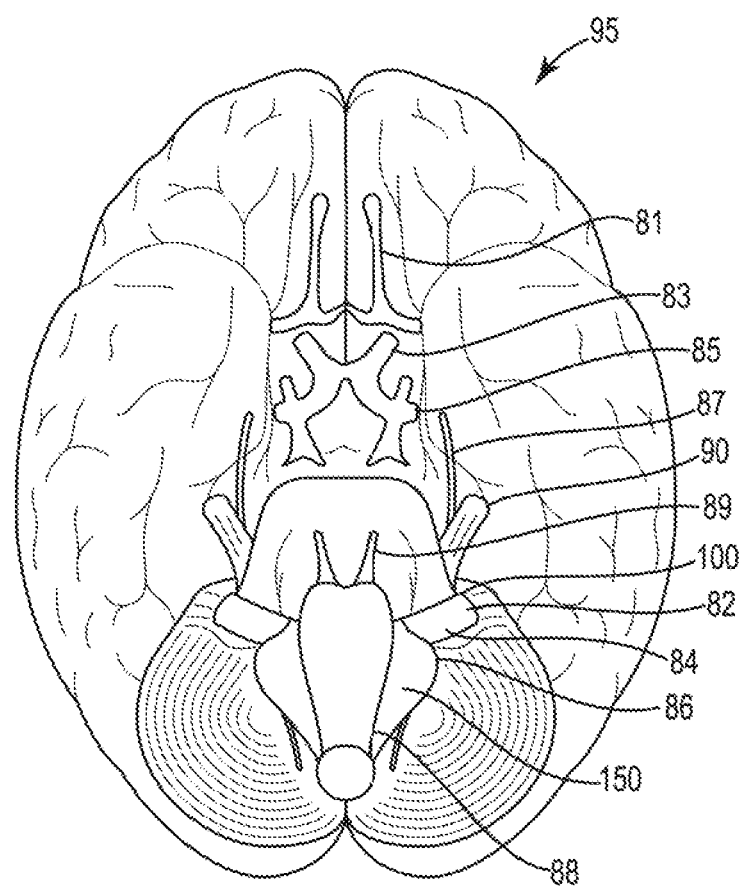
FIG. 13 shows an inferior view of the human brain 95 and the locations of various cranial nerves associated therewith.

FIG. 13 shows human brain 95 and the external locations of various cranial nerves 80 emerging therefrom or entering therein; namely: olfactory nerves 81, vestibulocochlear nerves 82, optic nerves 83, glossopharyngeal nerves 84, oculomotor nerves 85, vagus nerves 86, trochlear nerves 87, spinal accessory nerves 88, abducens nerves 89, trigeminal nerves 90, facial nerves 100, and hypoglossal nerves 150. One aspect of the various embodiments described and disclosed herein, is that lead 18 and electrodes 39 can be placed much closer to a target cranial nerve than is possible using an external TENS system simply because lead 18 is located beneath the skin and can be placed much more closely to the target nerve than is possible with a TENS electrode. Consequently, electrical stimulation can be provided to a much smaller nerve target region, which as a result provides superior therapeutic results owing to the more focused electrical filed being provided to the target cranial nerve.

Figure 14:
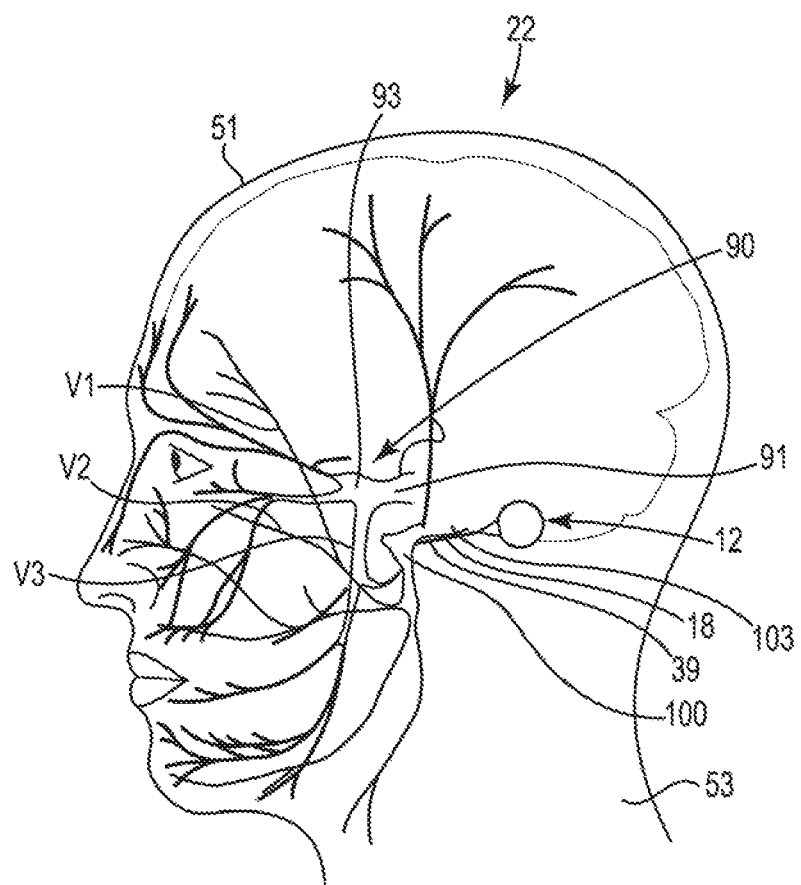
FIG. 14 shows human brain 95 and the external locations of various cranial nerves 80 emerging therefrom or entering therein.
Figure 15:
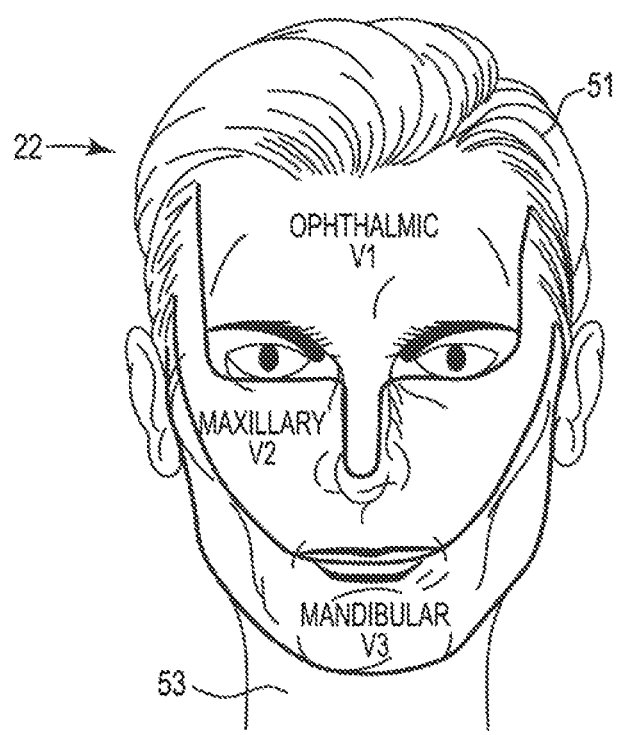
FIG. 15 shows patient 22, and patient's head 51 and neck 53, along with zones of sensation or effect corresponding to facial nerves V1, V2, and V3 shown in FIG. 15.

FIG. 14 shows a head 51 and neck 53 of a patient 22, and the locations of various facial nerves 100 and trigeminal nerves 90 thereon, Facial nerve branches V1, V2 and V3 are shown, as well as other portions and branches of the facial nerves 100. Posterior auricle nerve 103 located beneath patient 22's ear is also shown in FIG. 14. Trigeminal nerve root 91 (which is connected to the trigeminal nerve nucleus) and trigeminal gasserian ganglion 93 are also shown in FIG. 14. One nerve target, and depending on the precise electrical stimulation therapy to be delivered, along with all the other facial nerves and trigeminal nerves shown in FIG. 14, for treating a mood disorder or mood affective disorder, is posterior auricle nerve 103. For illustrative purposes, IS 12 and lead 18 are shown situated in proximity to nerve 103 so as to deliver electrical stimulation therapy thereto. As described above, CP 14, PP 16 and/or device 33 may be is employed to set up and control the electrical stimulation parameters of IS 12. Note that the relative sizes of IS 12 and patient's head 51 shown in FIG. 15 are merely illustrative and not necessarily to scale. IS 12 can be configured to be very small, and far smaller than conventional implantable pulse generators and their corresponding leads, more about which is said below.

FIG. 15 shows patient 22, and patient's head 51 and neck 53, along with zones of sensation or effect corresponding to facial nerves V1, V2, and V3 shown in FIG. 15. The therapy delivered by IS 12, and the location of implantation of IS 12 within head 51 or neck 53 of patient 22, may be selected in accordance with the illustrated ophthalmic (V1), maxillary (V2), and mandibular (V3) zones.

Figure 16:
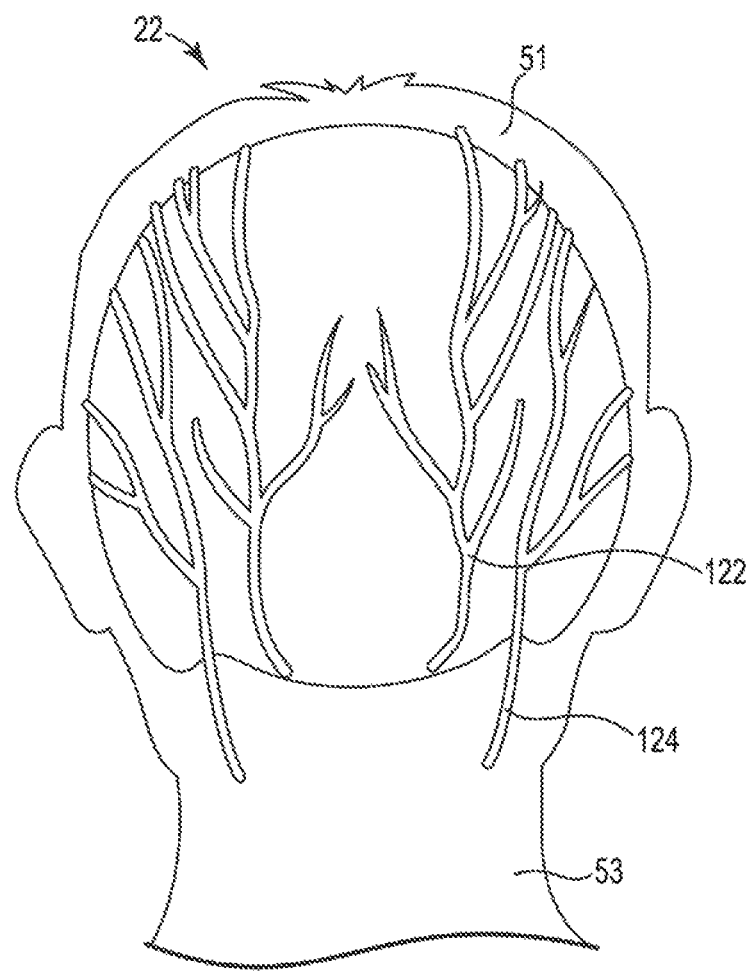
FIG. 16 shows the posterior of patient 22's head 51 and neck 53, and occipital nerves 122 (greater occipital nerves and their branches) and 124 (lesser occipital nerves and their branches)

FIG. 16 shows the rear of patient 22's head 51 and neck 53, and occipital nerves 122 (greater occipital nerves and their branches) and 124 (lesser occipital nerves and their branches). Nerves 122 and 124 may also be target nerves for IS 12 and lead 18 to electrically stimulate and thereby provide therapy for mood disorders and mood affective disorders.

Figure 17:
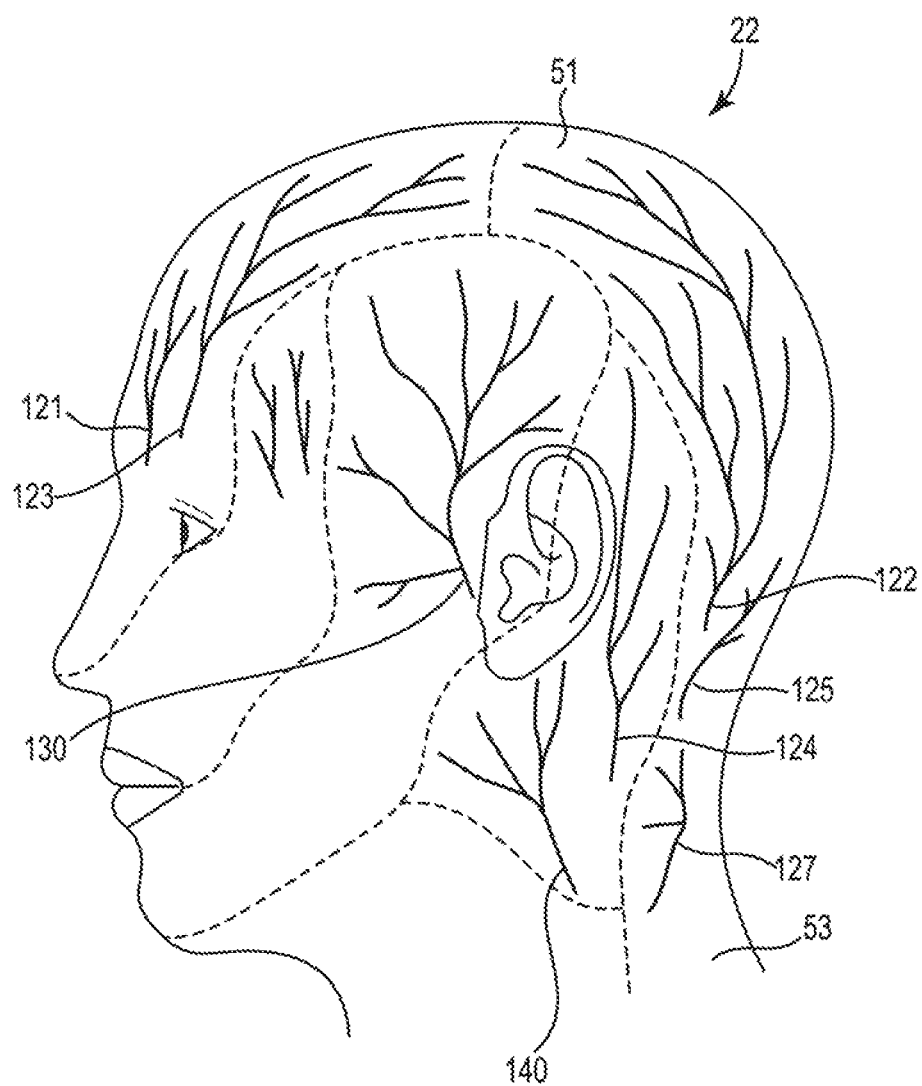
FIG. 17 shows a lateral view of patient 22's head 51 and neck 53, and the locations of various cranial nerve zones therein.

FIG. 17 shows a side view of patient 22's head 51 and neck 53, and the locations of various cranial nerve zones therein, including zones corresponding to: (a) a zone containing occipital nerves 122, 124 and 125, and C4 nerve 127; (b) a zone containing great auricular nerve 140; (c) a zone containing auriculotemporal nerve 130; (d) a zone containing supratrochlear nerve 121 and supraorbital nerve 123. IS 12 and corresponding lead 18 may be implanted beneath patient's skin 153 in operative relationship and location to electrically stimulate any of such cranial nerves 80 in any of such zones, depending on the specific therapy that is to be delivered, to treat the patient's mood disorder or mood affective disorder.

Figure 18:
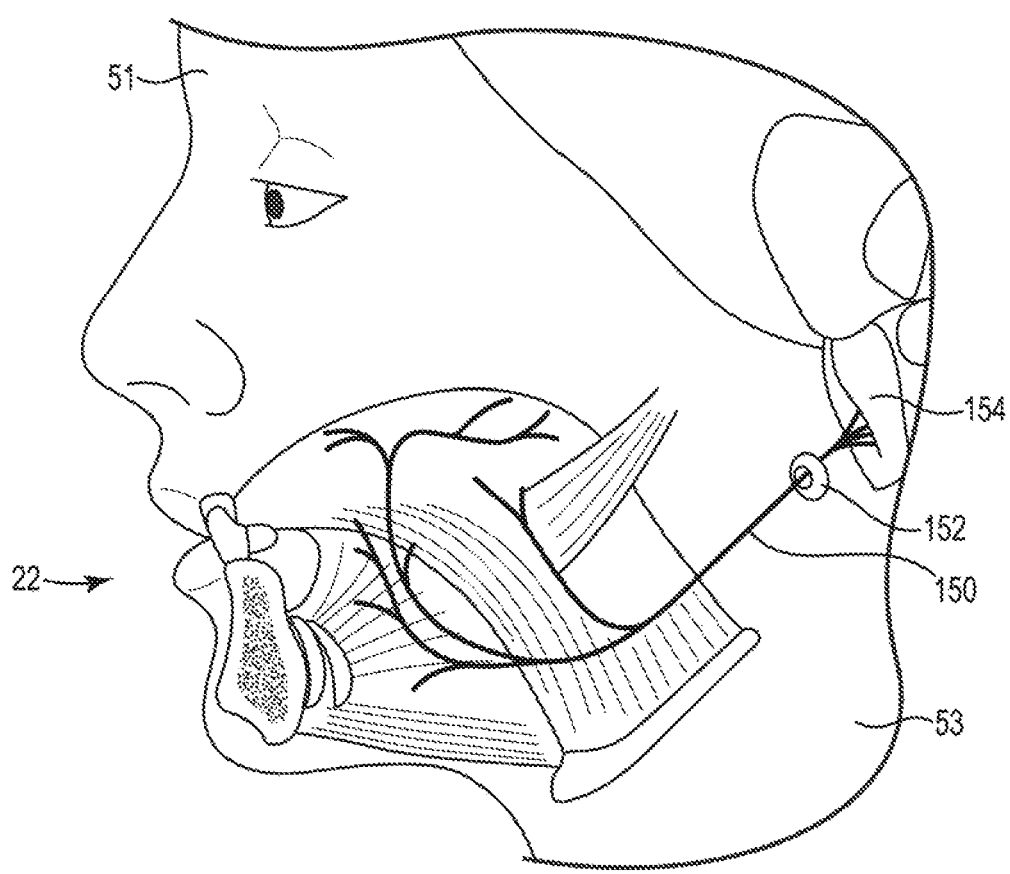
FIG. 18 shows patient 22 and patient's head 51 and neck 53, as well as hypoglossal nerve 150 and its branches and portions.

FIG. 18 shows patient 22 and patient's head 51 and neck 53, as well as hypoglossal nerve 150 and its branches and portions, including hypoglossal canal 152 and medulla oblongata 154. IS 12 and corresponding lead 18 may be implanted beneath patient's skin 153 in operative relationship and location to electrically stimulate any of such cranial nerves 80 in any of such zones, depending on the specific therapy that is to be delivered, to treat the patient's mood disorder or mood affective disorder.

Figure 19:
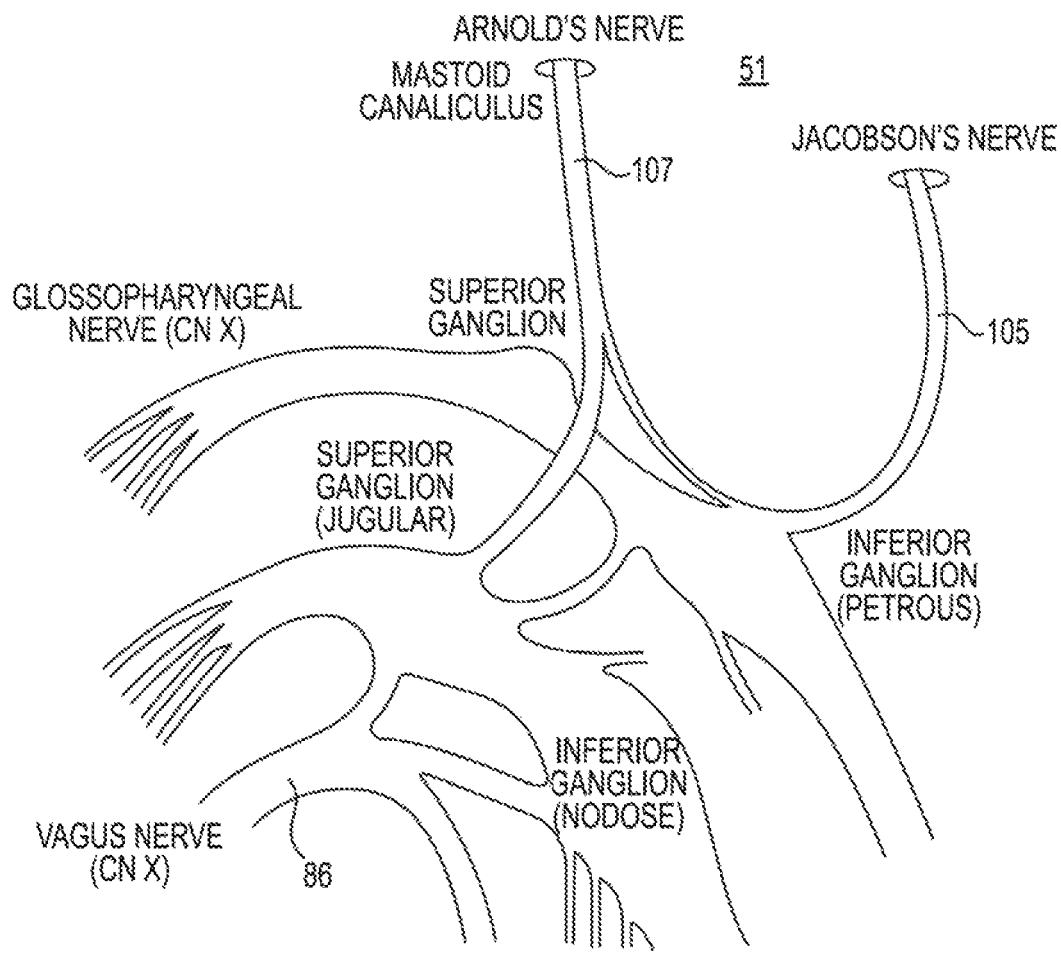
FIG. 19 shows portions of vagus nerve 86 and branches thereof connected to various cranial nerves 80 in patient's head 51 and neck 53.

FIG. 19 shows portions of vagus nerve 86 and branches thereof that are connected to various cranial nerves 80 in patient's head 51 and neck 53. These nerves and nerve branches of the vagus nerve include Arnold's Nerve 107 (which is connected to nerve 103), Jacobson's Nerve (or tympanic nerve) 105, vagus nerve CN X, glossopharyngeal nerve CN X, and others. IS 12 and corresponding lead 18 may be implanted beneath patient's skin 153 in operative relationship and location to electrically stimulate any of such cranial nerves 80 or vagus nerves 86, depending on the specific therapy that is to be delivered, to treat the patient's mood disorder or mood affective disorder. The auricular branch of vagus nerve 86 is Arnold's nerve 107, the eponymous name of the auricular branch, also known as the mastoid branch, of the vagus nerve (CN X). This nerve may be stimulated as a diagnostic or therapeutic technique to treat mood or mood affective disorders.

In some embodiments, one or more stimulation parameters of nerve stimulation signals comprise one or more of: (a) frequencies ranging between about 2 Hz and about 100 Hz; (b) frequencies ranging between about 2 Hz and about 75 Hz; (c) frequencies ranging between about 4 Hz and about 50 Hz; (d) frequencies ranging between about 5 Hz and about 25 Hz; (e) frequencies ranging between about 7 Hz and about 100 Hz; (f) voltage ranging between about 0.1 mV and about 30 V; (g) current ranging between about 0.1 mA and about 30 mA; pulse width ranging between about 20 μsec and about 1000 μsec. The first stimulation signal may also be provided as a constant voltage signal or a constant current signal.

In various embodiments, one or more stimulation parameters of the nerve stimulation signals may also be provided as constant voltage signals, constant current signals, triangular signals, biphasic signals, triphasic signals, chirp or swept signals, standard rectangular pulse signals, burst signals, and so on. Tapering of signals using, for example, Hanning, Hamming, and/or Blackman windowing techniques, may also be employed.

In further embodiments, the nerve stimulation signals are delivered to the one or more target nerves for periods of time ranging between about 60 seconds and about 180 minutes. In various embodiments, nerve stimulation signals are delivered to the one or more target nerves in bursts ranging between about 20 seconds and about 2 hours in duration. Such bursts can be delivered sequentially.

Therapy sessions can be adjusted or modified as required over the multi-day or multi-month time period over which the nerve stimulation signals are delivered to the patient. For example, the stimulation parameters of the nerve stimulation therapy sessions can be changed or modified as a day, or the multi-day or multi-month time period, progresses. Nerve stimulation therapy sessions can be shortened as the patient's mood or mood affective disorder symptoms are reduced.

In still further embodiments, electrodes 39 on lead(s) 18 may also be employed not only to stimulate targeted nerve bundles or nerves, but also to sense depolarization and repolarization signals originating from the targeted nerve bundles or tissue in proximity thereto. These sensed signals may in turn be employed by programming instructions loaded and circuitry disposed in IS 12 to process the sensed signals, and then determine whether or not the stimulation parameters of the nerve stimulation signals should be adjusted, thereby forming a feedback control loop for peripheral nerve stimulation.

It will now be seen that the various systems, devices, components and methods disclosed and described herein are capable of providing effective therapies to patients having different types of mood or mood affective disorders. Note, however, that the systems, devices, components, and methods disclosed and described herein are not limited to treating mood or mood affective disorders by stimulating one or more cranial nerves, and instead may be employed to treat, by way of non-limiting example, post-traumatic stress disorder (PTSD), epilepsy, drug or opioid addiction, tinnitus, Parkinson's disease, Alzheimer's disease, dementia, chronic balance deficit due to mild-to-moderate traumatic brain injury, movement disorders, attention or memory dysfunction associated with traumatic brain injury, sleep apnea (by, for example stimulating the hypoglossal or other cranial nerve(s) disclosed and described herein), and/or to modulate the activity of one or more targeted brain regions (by, for example, stimulating one or more the trigeminal nerves), What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing description and disclosure outline features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems in delivering cost-effective therapies to patients suffering from mood and mood affective disorders.

I claim:

1. An implantable neurostimulator configured to electrically stimulate one or more cranial nerves in a head or neck of a patient to treat a mood disorder or mood affective disorder of the patient, comprising:
    a hermetically sealed flexible housing;
    one or more flex circuits comprising one or more electrical conductors;
    pulse generation circuitry operably connected to the one or more flex circuits;
    at least one medical electrical lead comprising at least one stimulation electrode, the lead being operably connected to the pulse generation circuitry through at least one of the one or more electrical conductors of the one or more flex circuits, at least portions of the lead being formed on or in, or forming a portion of, the one or more flex circuits; and
    at least one of power, energy and electrical charge receiving circuitry operably connected to the pulse generation circuitry and configured to receive power, energy or electrical charge signals transcutaneously from an external power source and external power transmitting circuitry associated therewith;
    wherein the lead comprises proximal and distal portions, the at least one stimulation electrode is disposed distally from the proximal portion of the lead, the pulse generation circuitry, the power, energy and electrical charge receiving circuitry, and at least portions of the one or more flex circuits are disposed within the flexible housing, the implantable neurostimulator is sized, shaped and configured to be implanted in the head or neck of the patient beneath the patient's skin and positioned adjacent to, in contact with, or in operative positional relationship to, the one or more target cranial nerves, and further wherein the implantable neurostimulator and the lead thereof are sized, shaped and configured to electrically stimulate one or more of a facial nerve or portion thereof, a trigeminal nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an olfactory nerve or portion thereof, an optic nerve or portion thereof, an oculomotor nerve or portion thereof, and a spinal accessory nerve or portion thereof, a vestibulocochlear nerve or portion thereof, and a spinal accessory nerve or portion thereof.

2. The implantable neurostimulator of claim 1, wherein the mood disorder or mood affective disorder is one or more of depression, a depressive disorder, insomnia, sadness, mania, bipolar disorder, manic depression, bipolar affective disorder, postpartum depression, seasonal affective disorder (SAD), cyclothymic disorder, premenstrual dysphoric disorder, persistent depressive disorder (dysthymia), disruptive mood dysregulation disorder, depression related to medical illness, and depression induced by substance use or medication.

3. The implantable neurostimulator of claim 1, wherein the one or more flex circuits comprise a polyimide substrate.

4. The implantable neurostimulator of claim 1, wherein when the external power source is positioned over and sufficiently close to the implantable neurostimulator, energy is transferred transcutaneously to the power, energy and electrical charge receiving circuitry, thereby triggering and maintaining the operation of pulse generation circuitry only so long as the external power source is held in sufficiently close proximity thereto.

5. The implantable neurostimulator of claim 1, wherein the sealed housing has a thickness ranging between 0.1 inches and 0.4 inches.

6. The implantable neurostimulator of claim 1, wherein the sealed housing has a diameter ranging between 0.05 inches and 0.8 inches.

7. The implantable neurostimulator of claim 1, wherein the sealed housing comprises a flexible polymer configured to conform to at least one of a shape of the patient's skull or overlying skin.

8. The implantable neurostimulator of claim 7, wherein the flexible polymer is a thermosettable or shapeable material that can be formed into and will retain a desired shape or curvature.

9. The implantable neurostimulator of claim 1, wherein the distal portion of the lead has a length extending beyond the housing ranging between 0.1 inches and 4 inches.

10. The implantable neurostimulator of claim 1, wherein the distal portion of the lead has a width beyond the housing that ranges between 0.01 inches and 0.05 inches.

11. The implantable neurostimulator of claim 1, wherein the pulse generation circuitry and the power, energy and electrical charge receiving and storage circuitry are potted within the housing using a medical grade polymer.

12. The implantable neurostimulator of claim 1, wherein the at least one lead, the pulse generation circuitry, and the power, energy and electrical charge receiving and storage circuitry are mounted on or in, or formed as a portion of, a single flex circuit or flex circuit substrate.

13. The implantable neurostimulator of claim 1, wherein the lead has a length extending beyond the housing ranging between 0.1 inches and 4 inches.

14. The implantable neurostimulator of claim 1, wherein the power, energy and electrical charge receiving circuitry further comprises electrical charge storage circuitry.

15. The implantable neurostimulator of claim 1, wherein the power, energy and electrical charge receiving circuitry further comprises one or more internal induction coils configured to receive electrical power transcutaneously from one or more corresponding external induction coils.

16. The implantable neurostimulator of claim 1, wherein the power, energy or electrical charge receiving circuitry further comprises one or more wireless, RF, acoustic, piezoelectric, thin film bulk wave acoustic resonators (FBAR), or microwave energy receiving circuits.

17. The implantable neurostimulator of claim 1, wherein the pulse generation circuitry is configured to deliver stimulation signals comprising one or more of: (a) frequencies ranging between 2 Hz and 100 Hz; (b) frequencies ranging between 2 Hz and 75 Hz; (c) frequencies ranging between 4 Hz and 50 Hz; (d) frequencies ranging between about 5 Hz and about 25 Hz; (e) frequencies ranging between 7 Hz and 100 Hz; (f) frequencies ranging between 100 Hz and 10,000 Hz; (g) frequencies ranging between 100 Hz and 5,000 Hz; (h) frequencies ranging between 100 Hz and 2,000 Hz; (i) frequencies ranging between 100 Hz and 1,000 Hz; (j) frequencies ranging between 200 Hz and 750 Hz; (k) voltages ranging between 0.1 mV and 30 V; (g) currents ranging between 0.1 mA and 30 mA; (h) pulse widths ranging between 20 μsec and 1000 μsec; (i) durations or periods of time ranging between 30 seconds and 2 hours, 5 minutes and 1 hour, and 10 minutes and 45 minutes.

18. A system configured to electrically stimulate one or more cranial nerves in a head or neck of a patient to treat a mood disorder or mood affective disorder of the patient, comprising:

an implantable neurostimulator comprising an hermetically sealed flexible housing, one or more flex circuits comprising one or more electrical conductors; pulse generation circuitry operably connected to the one or more flex circuits; at least one medical electrical lead comprising at least one stimulation electrode, the lead being operably connected to the pulse generation circuitry through at least one of the one or more electrical conductors of the one or more flex circuits, at least portions of the lead being formed on or in, or forming a portion of, the one or more flex circuits; and at least one of power, energy and electrical charge receiving circuitry operably connected to the pulse generation circuitry and configured to receive power, energy or electrical charge signals transcutaneously from an external power source and external power transmitting circuitry associated therewith; wherein the lead comprises proximal and distal portions, the at least one stimulation electrode is disposed distally from the proximal portion of the lead, the pulse generation circuitry, the power, energy and electrical charge receiving circuitry, and at least portions of the one or more flex circuits are disposed within the flexible housing, the implantable neurostimulator is sized, shaped and configured to be implanted in the head or neck of the patient beneath the patient's skin and positioned adjacent to, in contact with, or in operative positional relationship to, the one or more target cranial nerves, and further wherein the implantable neurostimulator and the lead thereof are sized, shaped and configured to electrically stimulate one or more of a facial nerve or portion thereof, a trigeminal nerve or portion thereof, a hypoglossal nerve or portion thereof, a cranial portion of a vagus nerve, a glossopharyngeal nerve or portion thereof, an auricular branch of the vagus nerve or portion thereof, a tympanic branch of the vagus nerve or portion thereof, a superior ganglion branch of the vagus nerve or portion thereof, an olfactory nerve or portion thereof, an optic nerve or portion thereof, an oculomotor nerve or portion thereof, an abducens nerve or portion thereof, a vestibulocochlear nerve or portion thereof, and a spinal accessory nerve or portion thereof;

an external energy supply device configured to transmit energy transcutaneously through the skin of the patient to the implantable neurostimulator, and a controller or programmer configured to permit a health care provider or the patient to set, adjust, or change at least one of operational and stimulation parameters of the implantable neurostimulator.

19. The system of claim 18, wherein the external energy supply device comprises one or more batteries and one or more transmitting coils operably connected to the one or more batteries and configured to provide electromagnetic energy transcutaneously to one or more receiving coils included in or operably connected to the power, energy and electrical charge receiving circuitry of the neurostimulator.

20. The system of claim 18, wherein the external energy supply device comprises wireless, RF, acoustic, piezoelectric, thin film bulk wave acoustic resonator (FBAR), or microwave transmitter circuitry configured to transmit energy transcutaneously through the skin of the patient to the power, energy and electrical charge receiving circuitry of the implantable neurostimulator.

21. The system claim 18, wherein the mood disorder or mood affective disorder is one or more of depression, a depressive disorder, insomnia, sadness, mania, bipolar disorder, manic depression, bipolar affective disorder, postpartum depression, seasonal affective disorder (SAD), cyclothymic disorder, premenstrual dysphoric disorder, persistent depressive disorder (dysthymia), disruptive mood dysregulation disorder, depression related to medical illness, and depression induced by substance use or medication.

22. The system of claim 18, wherein the one or more flex circuits comprise a polyimide substrate.

23. The system claim 18, wherein the sealed housing has a thickness ranging between 0.1 inches and 0.4 inches.

24. The system claim 18, wherein the sealed housing has a diameter ranging between 0.05 inches and 0.8 inches.

25. The system claim 18, wherein the sealed housing comprises a flexible polymer configured to conform to at least one of a shape of the patient's skull or overlying skin.

26. The system claim 25, wherein the flexible polymer is a thermosettable or shapeable material that can be formed into and will retain a desired shape or curvature.

27. The system claim 18, wherein the distal portion of the lead has a length extending beyond the housing ranging between 0.1 inches and 4 inches.

28. The system claim 18, wherein the distal portion of the lead has a width beyond the housing that ranges between 0.01 inches and 0.05 inches.

29. The system claim 18, wherein the pulse generation circuitry and the power, energy and electrical charge receiving and storage circuitry are potted within the housing using a medical grade polymer.

30. The system claim 18, wherein the at least one lead, the pulse generation circuitry, and the power, energy and electrical charge receiving and storage circuitry are mounted on or in, or formed as a portion of, a single flex circuit or flex circuit substrate.

31. The system claim 18, wherein the distal portion of the lead has a length extending beyond the housing ranging between 0.1 inches and 4 inches.

32. The system claim 18, wherein the power, energy and electrical charge receiving circuitry further comprises electrical charge storage circuitry.

33. The system claim 18, wherein the power-, energy and electrical charge receiving circuitry further comprises one or more internal induction coils configured to receive electrical power transcutaneously from one or more corresponding external induction coils.

34. The system claim 18, wherein the power, energy and electrical charge receiving circuitry further comprises one or more wireless, RF, acoustic, piezoelectric, thin film bulk wave acoustic resonators (FBAR), or microwave energy receiving circuits.

35. The system of claim 18, wherein the pulse generation circuitry is configured to deliver stimulation signals comprising one or more of: (a) frequencies ranging between 2 Hz and 100 Hz; (b) frequencies ranging between 2 Hz and 75 Hz; (c) frequencies ranging between 4 Hz and 50 Hz; (d) frequencies ranging between 5 Hz and 25 Hz; (e) frequencies ranging between 7 Hz and 100 Hz; (f) frequencies ranging between 100 Hz and 10,000 Hz; (g) frequencies ranging between 100 Hz and 5,000 Hz; (h) frequencies ranging between 100 Hz and 2,000 Hz; (i) frequencies ranging between 100 Hz and 1,000 Hz; (j) frequencies ranging between 200 Hz and 750 Hz; (k) voltages ranging between 0.1 mV and 30 V; (g) currents ranging between 0.1 mA and 30 mA; and (h) pulse widths ranging between 20 μsec and 1000 μsec, and (h) durations or periods of time ranging between 30 seconds and 2 hours, 5 minutes and 1 hour, and 10 minutes and 45 minutes.

\* \* \* \* \*